United States Patent
Sabourin et al.

(10) Patent No.: US 11,198,123 B2
(45) Date of Patent: Dec. 14, 2021

(54) CARTRIDGE DEVICE WITH BYPASS CHANNEL FOR MITIGATING DRIFT OF FLUID SAMPLES

(71) Applicant: Abbott Point of Care Inc., Princeton, NJ (US)

(72) Inventors: David Sabourin, Ottawa (CA); Alain Villeneuve, Kanata (CA); Bruce Hendry, Stittsville (CA); Jessica Chung, Ottawa (CA); Graham E. Garrett, Ottawa (CA); Vinoth Kumar Govindaraj, Nepean (CA); Katrina Petronilla Di Tullio, Stittsville (CA); Sheila Diane Ball, Kanata (CA)

(73) Assignee: Abbott Point of Care Inc., Princeton, NJ (US)

( * ) Notice: Subject to any disclaimer, the term of this patent is extended or adjusted under 35 U.S.C. 154(b) by 274 days.

(21) Appl. No.: 16/426,473

(22) Filed: May 30, 2019

(65) Prior Publication Data
US 2020/0001292 A1    Jan. 2, 2020

Related U.S. Application Data

(60) Provisional application No. 62/691,909, filed on Jun. 29, 2018.

(51) Int. Cl.
*B01L 3/00* (2006.01)
*A61B 10/00* (2006.01)

(52) U.S. Cl.
CPC ..... *B01L 3/50273* (2013.01); *B01L 3/502715* (2013.01); *A61B 10/0096* (2013.01);
(Continued)

(58) Field of Classification Search
CPC .......... A61B 10/0096; B01L 2200/027; B01L 2300/0636; B01L 2300/0816;
(Continued)

(56) References Cited

U.S. PATENT DOCUMENTS

| 6,084,660 A * | 7/2000 | Shartle ............... G01N 33/4905 |
| | | 356/246 |
| 2008/0026476 A1* | 1/2008 | Howell ............. B01L 3/502761 |
| | | 436/69 |

(Continued)

FOREIGN PATENT DOCUMENTS

| EP | 0803288 A2 * | 10/1997 | .......... B01L 3/50273 |
| WO | 2005114140 | 12/2005 | |
| WO | 2015019120 | 2/2015 | |

OTHER PUBLICATIONS

International Application No. PCT/US2019/034624, International Preliminary Report on Patentability, dated Jan. 7, 2021, 8 pages.
(Continued)

*Primary Examiner* — Jennifer Wecker
*Assistant Examiner* — Jonathan Bortoli
(74) *Attorney, Agent, or Firm* — Kilpatrick Townsend & Stockton LLP

(57) ABSTRACT

The present disclosure relates to analytical testing devices comprising microfluidics and methods for performing an assay on a fluid sample received within the microfluidics, and in particular, to mitigating drift of fluid samples over a sensor by incorporating a bypass channel into the microfluidics. For example, a test cartridge device is provided that includes a fluid sample entry port and holding chamber connected to a bifurcation junction of a sensor channel and a bypass channel. The sensor channel includes an upstream region and a downstream region, and an analyte sensor is in the upstream region. As a cross-sectional area of the bypass channel is greater than the cross-sectional area of the down-
(Continued)

stream region of the sensor channel, the bypass channel is a preferred path for excess sample flow and pressure, and thus sample drift above the analyte sensor is mitigated.

20 Claims, 26 Drawing Sheets

(52) U.S. Cl.
CPC . *B01L 2200/027* (2013.01); *B01L 2400/0481* (2013.01); *B01L 2400/088* (2013.01)

(58) Field of Classification Search
CPC ..... B01L 2300/0864; B01L 2400/0481; B01L 2400/084; B01L 2400/088; B01L 3/502715; B01L 3/50273; B01L 3/502746; G01N 33/86
See application file for complete search history.

(56) References Cited

U.S. PATENT DOCUMENTS

| | | |
|---|---|---|
| 2016/0091508 A1 | 3/2016 | Zhao et al. |
| 2016/0214108 A1 | 7/2016 | Solomon et al. |

OTHER PUBLICATIONS

International Application No. PCT/US2019/034624, "International Search Report and Written Opinion", dated Jul. 23, 2019, 12 pages.

\* cited by examiner

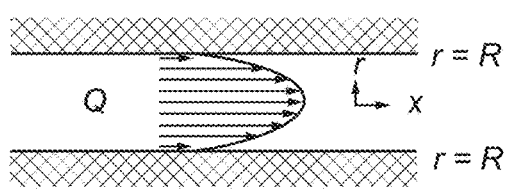
FIG. 2A
$R_H \propto L$
$A$ | $\eta$: fluidic viscosity
$C_{geometry}$: geometric coefficient
$R_H = C_{geometry} \eta \dfrac{L}{A^2}$
FIG. 2B
Hagen-Poiseuille Law: $\Delta p = p_+ - p_- = Q R_H$
FIG. 2C
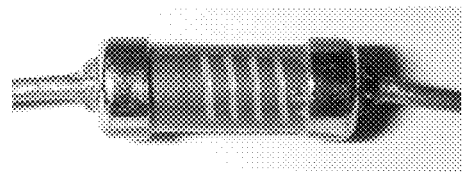
FIG. 2D
$R_E \propto l$
$A$ | $\rho_E$: resistivity [$\Omega$ m]
$R_E = \rho_E \dfrac{l}{A}$
FIG. 2E
Ohm's Law: $V = V_+ - V_- = I R_E$
FIG. 2F

| shape | | $R_{hyd}$ expression | $R_{hyd}$ [$10^{11} \frac{Pas}{m^3}$] |
|---|---|---|---|
| circle |  | $\frac{8}{\pi} \eta L \frac{1}{a^4}$ | 0.25 |
| ellipse |  | $\frac{4}{\pi} \eta L \frac{1 + (b/a)^2}{(b/a)^3} \frac{1}{a^4}$ | 3.93 |
| triangle |  | $\frac{320}{\sqrt{3}} \eta L \frac{1}{a^4}$ | 18.48 |
| two plates |  | $12 \eta L \frac{1}{h^3 w}$ | 0.40 |
| rectangle |  | $\frac{12 \eta L}{1 - 0.63(h/w)} \frac{1}{h^3 w}$ | 0.51 |
| square |  | $\frac{12 \eta L}{1 - 0.917 \times 0.63} \frac{1}{h^4}$ | 2.84 | a) Series
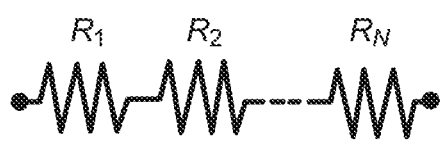
b) Parallel
FIG. 3A
FIG. 3B
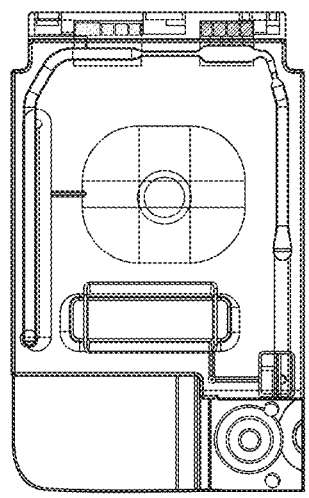
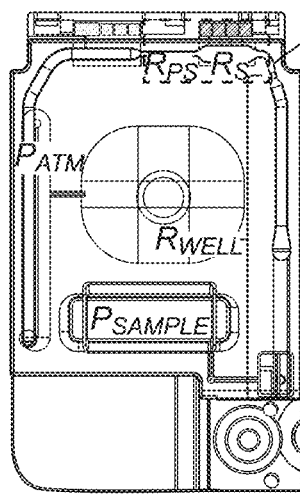
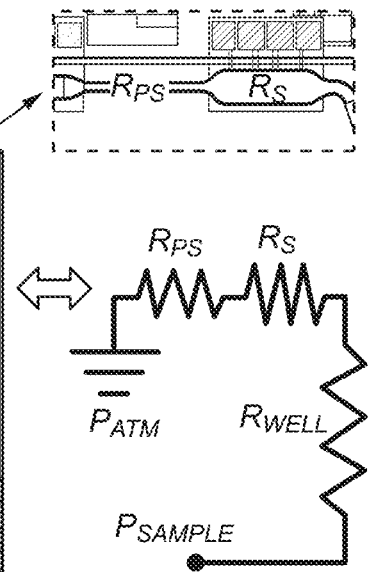
FIG. 4A
FIG. 4B
FIG. 4C

CARTRIDGE DEVICE WITH BYPASS CHANNEL FOR MITIGATING DRIFT OF FLUID SAMPLES

CROSS-REFERENCE TO RELATED APPLICATIONS

This application claims priority to U.S. Provisional Application No. 62/691,909, filed on Jun. 29, 2018, the entirety of which is incorporated herein by reference.

FIELD OF THE INVENTION

The present disclosure relates to analytical testing devices comprising microfluidics and methods for performing an assay on a fluid sample received within the microfluidics, and in particular, to mitigating drift of fluid samples over a sensor by incorporating a bypass channel into the microfluidics.

BACKGROUND

Point-of-care (POC) sample analysis systems are typically based on one or more re-usable hand-held analyzers (i.e., instruments or reading apparatus) that perform sample tests using a single-use disposable testing device, (e.g., a cartridge or strip) that contains analytical elements, (e.g., electrodes or optics) for sensing analytes such as pH, oxygen and glucose, as well as various types of proteins, enzymes and blood cells. The disposable testing device may include fluidic elements (e.g., channels or conduits for receiving and delivering the sample to sensing electrodes or optics), calibrant elements (e.g., aqueous fluids for standardizing the electrodes and optics with a known concentration of analyte), and dyes with known extinction coefficients for standardizing optics. The instrument or reading apparatus may contain electrical circuitry and other components for operating the electrodes or optics, making measurements, and performing computations. The instrument or reading apparatus may also have the ability to display results and communicate those results to laboratory and hospital information systems (LIS and HIS, respectively), for example, via a computer workstation or other data management system. Communication between the instrument or reading apparatus and a workstation, and between the workstation and a LIS or HIS, may be via, for example, an infrared link, a wired connection, wireless communication, or any other form of data communication that is capable of transmitting and receiving electrical information, or any combination thereof. A notable point-of-care system (The i-STAT® System, Abbott Point of Care Inc., Princeton, N.J.) is disclosed in U.S. Pat. No. 5,096,669, which is incorporated herein by reference in its entirety. The i-STAT® System comprises one or more disposable testing devices, operating in conjunction with a hand-held analyzer, for performing a variety of measurements on biological specimens such as blood.

One benefit of point-of-care sample testing systems is the elimination of the time-consuming need to send a sample to a central laboratory for testing. Point-of-care sample testing systems allow a nurse or doctor (user or operator), at the bedside of a patient, to obtain a reliable quantitative analytical result, comparable in quality to that which would be obtained in a laboratory. In operation, the nurse selects a testing device with the required panel of tests, draws a biological sample from the patient, dispenses the biological sample into the testing device, optionally seals the testing device, and inserts the testing device into the instrument or reading apparatus. While the particular order in which the steps occur may vary between different point-of-care systems and providers, the intent of providing rapid sample test results close to the location of the patient remains the same. The instrument or reading apparatus then performs a test cycle, i.e., all the other analytical steps required to perform the tests. Such simplicity gives the doctor quicker insight into a patient's physiological status and, by reducing the turnaround time for diagnosis or monitoring, enables a quicker decision by the doctor on the appropriate treatment, thus enhancing the likelihood of a successful patient outcome.

Point-of-care sample testing systems typically include an instrument or analyzer configured to perform sample tests using single-use disposable testing devices for the determination of analytes in biological samples. The type of sample tests performed may vary and can be implemented using one or more disposable testing devices including, for example, a quantitative testing device (e.g., an electrochemical assay). Electrochemical detection involves the use of a working electrode (e.g., an amperometric electrode) and a reference electrode (e.g., a counter reference electrode), whereby a constant potential is applied to the working electrode leading to an oxidation-reduction (redox) reaction that can be quantified as a recordable electric current. Electrochemical sensors have found widespread use in the development of point-of-care (POC) and self-test devices, as exemplified by the development of glucose test strips, as they are simple to interface with electronic instruments and reduce device costs. Devices, such as the i-STAT® system (see, e.g., U.S. Pat. Nos. 7,977,106 and 9,903,877, the entireties of which are incorporated herein by reference), have employed electrogenic substrates that result in the formation of an electrochemically detectable cleavage product that is proportional to a target analyte of interest such as thrombin activity. These devices are then configured to return a quantitative result such as clotting time based on a measure of thrombin activity to allow comparisons with standard clotting.

However, point of care assay systems configured to perform the aforementioned electrochemical assays may comprise the reagent and substrate printed in a dissolvable form on or near sensors, for example, in a micro-environment arrangement. Micro-environment sensor structures comprise one or more reagents and one or more substrates in any of a number of different arrangements such that the introduction of the fluid sample, (e.g., whole blood), to the one or more reagents and the one or more substrates is localized to the one or more sensors. During analysis, the sample is positioned by a mechanical process over the micro-environment sensor structure for a predetermined amount of time to dissolve the reagent and substrate into the sample, and perform electrochemical detection using the one or more sensors. This arrangement of having the reagent and substrate printed in this form in combination with the predetermined amount of time required for dissolving the reagent and substrate and performance of the electrochemical detection relies on limiting sample drift over the sensors. Accordingly, the need exists for improved point-of-care cartridge or testing device design that limit drift over the sensors and allow electrochemical analysis to be performed using micro-environment sensor structures provided in a single point-of-care cartridge or testing device.

BRIEF SUMMARY

In various embodiments, a test cartridge device is provided for measuring an analyte in a fluid sample, the test cartridge device comprising: a fluid sample entry port for receiving the fluid sample; a holding chamber fluidically connected to the entry port; a bifurcation junction fluidically connected to the holding chamber; a first channel splitting off from the bifurcation junction, the first channel comprising an upstream region and a downstream region; a sensor positioned within the upstream region for measuring the analyte in the fluid sample; a second channel splitting off from the bifurcation junction; and a recombination junction that rejoins the first channel and the second channel into a third channel. A cross-sectional area of the upstream region is greater than a cross-sectional area of the downstream region, and a cross-sectional area of the second channel is less than the cross-sectional area of the upstream region and greater than the cross-sectional area of the downstream region.

In some embodiments, a ratio of the cross-sectional area of the upstream region to the cross-sectional area of the downstream region is in a range from 4:1 to 50:1. In some embodiments, a ratio of the cross-sectional area of the second channel to the cross-sectional area of the upstream region is in a range from 0.5:1 to 1:125 and a ratio of the cross-sectional area of the second channel to the cross-sectional area of the downstream region is in a range from 1.2:1 to 100:1.

Optionally, the cross-sectional area of the upstream region is in a range from 0.1 mm$^2$ to 20 mm$^2$. Optionally, the cross-sectional area of the downstream region is in a range from 0.1 mm$^2$ to 10 mm$^2$. Optionally, the cross-sectional area of the second channel is in a range from 0.1 mm$^2$ to 15 mm$^2$. The volume of the upstream region may be in a range from 0.5 µL to 50 µL. The volume of the downstream region may be in a range from 0.5 µL to 50 µL. The volume of the second channel may be in a range from 0.5 µL to 50 µL. A total volume of the first channel from the bifurcation junction to the recombination junction may be in a range from 0.5 µL to 50 µL.

In some embodiments, the third channel comprises a vent to an atmosphere outside of the test cartridge device. In some embodiments, the test cartridge device further comprises a lead channel that joins the bifurcation junction with the holding chamber. In some embodiments, the test cartridge device further comprises a constriction or capillary stop at a terminus of the holding chamber. Optionally, the lead channel defines a channel area between the constriction or capillary stop and the bifurcation junction.

In some embodiments, the sensor comprises one or more transducers coated with a polymer layer, the polymer layer is a porous support layer that comprises immobilized therein a thrombin-cleavable peptide, and the thrombin-cleavable peptide comprises a detectable moiety linked by a thrombin-cleavable amide bond to a polypeptide sequence that is non-reactive with blood proteases other than thrombin. The test sensor may be a prothrombin time (PT) sensor, an activated partial thromboplastin time (aPTT) sensor, or an activated clotting time (ACT) sensor.

In various embodiments, a test cartridge device is provided for measuring an analyte in a fluid sample, the test cartridge device comprising a fluid sample entry port and holding chamber connected to a bifurcation junction of a first channel and a second channel. The first channel comprises an upstream region and a downstream region, at least one analyte sensor is in the upstream region, a cross-sectional area of the upstream region of the first channel is larger than a cross-sectional area of the downstream region the first channel, a cross-sectional area of the second channel is less than the cross-sectional area of the upstream region of the first channel, and the cross-sectional area of the second channel is greater than the cross-sectional area of the downstream region of the first channel.

In some embodiments, the first channel and the second channel are connected at a recombination junction to a third channel. In other embodiments, the downstream region may terminate at a first terminal end and the second channel terminates at a second terminal end. Optionally, a capillarity of the upstream region of the first channel is greater than a capillarity of the second channel, and a capillarity of the downstream region of the first channel is less than the capillarity of the second channel.

In some embodiments, flow rate of the fluid sample through the first channel and the second channel is substantially independent of one or more properties including: (i) viscosity in a range from about 0.8 mPa·s to about 3 mPa·s; (ii) total cellular content in a range from 0 to 80%; or (iii) hematocrit in a range from 0 to 80%. Optionally, the test cartridge device further comprises a pump connected to the holding chamber for moving the fluid sample from the holding chamber to the first channel and the second channel.

In some embodiments, the at least one analyte sensor is a prothrombin time (PT) micro-environment sensor. In other embodiments, the at least one analyte sensor is an activated partial thromboplastin time (aPTT) micro-environment sensor. In yet other embodiments, the at least one analyte sensor is an activated clotting time (ACT) micro-environment sensor. In certain embodiments, the at least one analyte sensor comprises a prothrombin time (PT) micro-environment sensor and an activated partial thromboplastin time (aPTT) micro-environment sensor.

In some embodiments, the cross-sectional area of the upstream region is in a range from 0.1 mm$^2$ to 20 mm$^2$. In some embodiments, the cross-sectional area of the downstream region is in a range from 0.1 mm$^2$ to 10 mm$^2$. In some embodiments, the cross-sectional area of the second channel is in a range from 0.1 mm$^2$ to 15 mm$^2$. In some embodiments, a length of the upstream region is in a range from 1 mm to 25 mm. In some embodiments, a length of the downstream region is in a range from 5 mm to 30 mm. In some embodiments, a length of the second channel is in a range from 1 mm to 30 mm.

In some embodiments, the entry port has a closeable seal. In some embodiments, the test cartridge device further comprises a trapped segment of air between a terminus of the downstream region of the first channel and the recombination junction. Optionally, a volume of the trapped segment of air is in a range from 0.1 µL to 10 µL. A volume of the holding chamber may be in a range from 5 µL to 200 µL.

In some embodiments, the test cartridge device further comprises a plastic housing comprising a first plastic member and a second plastic member joined by a double-sided adhesive tape gasket. In some embodiments, the first channel, the second channel, and the bifurcation junction are defined by one or more of the first plastic member, the second plastic member, and the double-sided adhesive tape gasket. In some embodiments, the test cartridge is engaged with an instrument, and the instrument comprises: (i) an actuator to apply a force to the pump, and (ii) an electrical connector in electrical contact with the at least one analyte sensor.

In some embodiments, the fluid sample is blood, diluted blood, plasma, diluted plasma, serum, diluted serum, urine, diluted urine, saliva, diluted saliva, an aqueous control fluid, or a calibrant fluid.

In various embodiments, a coagulation test cartridge device is provided for measuring a prothrombin time (PT)

and an activated partial thromboplastin time (aPTT) in a fluid sample, the coagulation test cartridge device comprising: a fluid sample entry port and holding chamber connected to a bifurcation junction of a first channel and a second channel. The first channel comprises an upstream region and a downstream region, a PT sensor and an APTT sensor are located in the upstream region, a cross-sectional area of the upstream region of the first channel is larger than a cross-sectional area of the downstream region of the first channel, a cross-sectional area of the second channel is less than the cross-sectional area of the upstream region of the first channel, and the cross-sectional area of the second channel is greater than the cross-sectional area of the downstream region of the first channel.

In various embodiments, a test system is provided comprising: an instrument and a test cartridge device electrically connected to the instrument. The test cartridge device comprises a fluid sample entry port and a holding chamber connected to a bifurcation junction of a first channel and a second channel, the first channel comprises an upstream region and a downstream region, at least one analyte sensor is in the upstream region, a cross-sectional area of the upstream region of the first channel is larger than a cross-sectional area of the downstream region of the first channel, a cross-sectional area of the second channel is less than the cross-sectional area of the upstream region of the first channel, and the cross-sectional area of the second channel is greater than the cross-sectional area of the downstream region of the first channel.

In various embodiments, a method is provided for measuring an analyte in a fluid sample, the method comprising: introducing the fluid sample through an entry port and into a holding chamber, where the fluid sample entry port and the holding chamber are connected to a bifurcation junction of a first channel and a second channel; activating a pump to create pressure to push the fluid sample from the holding chamber through the bifurcation junction into the first channel and the second channel, where initially the fluid sample preferentially fills the first channel because a cross-sectional area of the second channel is less than a cross-sectional area of an upstream region of the first channel, and once the upstream region of the first channel is filled with the fluid sample, then the fluid sample preferentially fills the second channel because the cross-sectional area of the second channel is greater than a cross-sectional area of a downstream region of the first channel; and performing an assay on the fluid sample in contact with a sensor in the upstream region of the first channel in order to measure the analyte in the fluid sample.

In some embodiments, the cross-sectional area of the upstream region of the first channel is larger than the cross-sectional area of the downstream region of the first channel.

In some embodiments, the pumped fluid sample in the first channel and the second channel stops short of a recombination junction of the first channel and the second channel. The pumped fluid sample in the second channel may reach the recombination junction before the pumped fluid sample in the first channel, which traps a segment of air between a terminus of the downstream region of the first channel and the recombination junction.

In some embodiments, the sensor is a prothrombin time (PT) micro-environment sensor, an activated partial thromboplastin time (aPTT) micro-environment sensor, or an activated clotting time (ACT) micro-environment sensor.

In some embodiments, the cross-sectional area of the upstream region is in a range from 0.1 mm$^2$ to 20 mm$^2$. In some embodiments, the cross-sectional area of the downstream region is in a range from 0.1 mm$^2$ to 10 mm$^2$. In some embodiments, the cross-sectional area of the second channel is in a range from 0.1 mm$^2$ to 15 mm$^2$. Optionally, a length of the upstream region is in a range from 1 mm to 25 mm. Optionally, a length of the downstream region is in a range from 5 mm to 30 mm. Optionally, a length of the second channel is in a range from 1 mm to 30 mm.

In some embodiments, the trapped segment of air has a volume in a range from 0.1 to 10 µL. A volume of the holding chamber may be in a range from 5 µL to 200 µL. In some embodiments, the fluid sample is blood, diluted blood, plasma, diluted plasma, serum, diluted serum, an aqueous control fluid, or a calibrant fluid.

In some embodiments, the method further comprises performing an additional assay on the fluid sample in contact with another sensor in the upstream region of the first channel in order to measure a different analyte in the fluid sample. The sensor may be a prothrombin time (PT) micro-environment sensor disposed in a first region of the upstream region of the first channel, and the another sensor may be an activated partial thromboplastin time (aPTT) micro-environment sensor in a second region of the upstream region of the first channel. In some embodiments, the method further comprises amending the fluid sample with a PT reagent in the first region and an aPTT reagent in the second region. In some embodiments, the method further comprises waiting a predetermined amount of time for the amended fluid sample to diffuse into a first thrombin-cleavable peptide, which is an immobilized PT substrate, in the first region and a second thrombin-cleavable peptide, which is an immobilized aPTT substrate, in the second region; and determining a PT using the PT sensor, and an aPTT using the aPTT sensor.

In some embodiments, the method further comprises determining arrival of the fluid sample at a position upstream of the sensor with a first portion of a conductivity sensor based on a first change in measured conductivity, and determining arrival of the fluid sample at a position downstream of the sensor with a second portion of the conductivity sensor based on a second change in measured conductivity.

In some embodiments, the method further comprises determining arrival of the fluid sample at a position upstream of the another sensor with a first portion of a conductivity sensor based on a first change in measured conductivity, and determining arrival of the fluid sample at a position downstream of the another sensor with a second portion of the conductivity sensor based on a second change in measured conductivity.

In various embodiments, a coagulation test cartridge device is provided for measuring a prothrombin time (PT) in a fluid sample, the coagulation test cartridge device comprising: a fluid sample entry port and holding chamber connected to a bifurcation junction of a first channel and a second channel. The first channel comprises an upstream region and a downstream region, a PT sensor is located in the upstream region, a cross-sectional area of the upstream region of the first channel is larger than a cross-sectional area of the downstream region of the first channel, a cross-sectional area of the second channel is less than the cross-sectional area of the upstream region of the first channel, and the cross-sectional area of the second channel is greater than the cross-sectional area of the downstream region of the first channel.

In various embodiments, a coagulation test cartridge device for measuring an activated partial thromboplastin time (aPTT) in a fluid sample, the coagulation test cartridge device comprising: a fluid sample entry port and holding chamber connected to a bifurcation junction of a first channel and a second channel. The first channel comprises an upstream region and a downstream region, an APTT sensor is located in the upstream region, a cross-sectional area of the upstream region of the first channel is larger than a cross-sectional area of the downstream region of the first channel, a cross-sectional area of the second channel is less than the cross-sectional area of the upstream region of the first channel, and the cross-sectional area of the second channel is greater than the cross-sectional area of the downstream region of the first channel.

In various embodiments, a test cartridge device for measuring an analyte in a fluid sample, the test cartridge device comprising: a fluid sample entry port for receiving the fluid sample; a holding chamber fluidically connected to the entry port; a bifurcation junction fluidically connected to the holding chamber; a first channel splitting off from the bifurcation junction, the first channel comprising an upstream region and a downstream region, where the downstream region terminates at a first terminal end; a sensor positioned within the upstream region for measuring the analyte in the fluid sample; and a second channel splitting off from the bifurcation junction, where the second channel terminates at a second terminal end. A cross-sectional area of the upstream region is greater than a cross-sectional area of the downstream region, and a cross-sectional area of the second channel is less than the cross-sectional area of the upstream region and greater than the cross-sectional area of the downstream region.

In some embodiments, a ratio of the cross-sectional area of the upstream region to the cross-sectional area of the downstream region is in a range from 4:1 to 50:1. In some embodiments, a ratio of the cross-sectional area of the second channel to the cross-sectional area of the upstream region is in a range from 0.5:1 to 1:125 and a ratio of the cross-sectional area of the second channel to the cross-sectional area of the downstream region is in a range from 1.2:1 to 100:1. In some embodiments, the cross-sectional area of the upstream region is in a range from 0.1 $mm^2$ to 20 $mm^2$. In some embodiments, the cross-sectional area of the downstream region is in a range from 0.1 $mm^2$ to 10 $mm^2$. In some embodiments, the cross-sectional area of the second channel is in a range from 0.1 $mm^2$ to 15 $mm^2$.

In some embodiments, a volume of the upstream region is in a range from 0.05 μL to 50 μL. In some embodiments, a volume of the downstream region is in a range from 0.5 μL to 50 μL. In some embodiments, a volume of the second channel is in a range from 0.5 μL to 50 μL. In some embodiments, a total volume of the first channel from the bifurcation junction to the first terminal end is in a range from 0.5 μL to 50 μL.

In some embodiments, the first channel further comprises a first vent to an atmosphere outside of the test cartridge device. The first vent may be positioned at the first terminal end. In some embodiments, the second channel comprises a second vent to the atmosphere outside of the test cartridge device. The second vent may be positioned at the second terminal end.

In some embodiments, the sensor comprises one or more transducers coated with a polymer layer, the polymer layer is a porous support layer that comprises immobilized therein a thrombin-cleavable peptide, and the thrombin-cleavable peptide comprises a detectable moiety linked by a thrombin-cleavable amide bond to a polypeptide sequence that is non-reactive with blood proteases other than thrombin. The test sensor may be a prothrombin time (PT) sensor, an activated partial thromboplastin time (aPTT) sensor, or an activated clotting time (ACT) sensor.

The foregoing, together with other features and embodiments will become more apparent upon referring to the following specification, claims, and accompanying drawings.

BRIEF DESCRIPTION OF THE DRAWINGS

The present invention will be better understood in view of the following non-limiting figures, in which:

FIGS. 2A-2G show characterization of microfluidic circuits and electrical circuits in accordance with various embodiments;

FIGS. 3A and 3B show equivalent hydraulic resistances for resistive elements connected in series and parallel in accordance with various embodiments;

FIG. 4A shows a conventional test cartridge device comprising a single sensor channel having a micro-environment sensor structure;

FIG. 4B shows typical fluidic circuit elements of a conventional test cartridge device;

FIG. 4C shows fluidic circuit elements modeled in a fluidic circuit;

DETAILED DESCRIPTION

In the following description, for the purposes of explanation, specific details are set forth in order to provide a thorough understanding of various embodiments described herein. However, it will be apparent that the various embodiments may be practiced without these specific details. The figures and description are not intended to be restrictive.

Introduction

The present disclosure relates to analytical testing devices comprising microfluidics and methods for performing an assay on a fluid sample received within the microfluidics, and in particular, to mitigating drift of fluid samples over a sensor by incorporating a bypass channel into the microfluidics. In various embodiments, a test cartridge device for measuring an analyte in a fluid sample is provided that includes an inlet chamber configured to receive the fluid sample (e.g., blood, plasma, serum, urine, saliva, cerebrospinal fluid, lysed cells, control, calibrant, or the like and modified and diluted forms thereof) and a channel (e.g., a conduit formed within a portion of the test cartridge device) fluidically connected to the inlet chamber and configured to receive the fluid sample from the inlet chamber. The channel may comprise a micro-environment sensor structure that is configured to operate in a localized manner to quantitatively detect a target analyte. For example, the channel may comprise a first micro-environment sensor and a second micro-environment sensor configured to operate in a localized manner and are capable of determining, respectively, a first diagnostic clotting time (e.g., PT) and a second diagnostic clotting time (e.g., aPTT) different from the first diagnostic clotting time.

Figure 1:
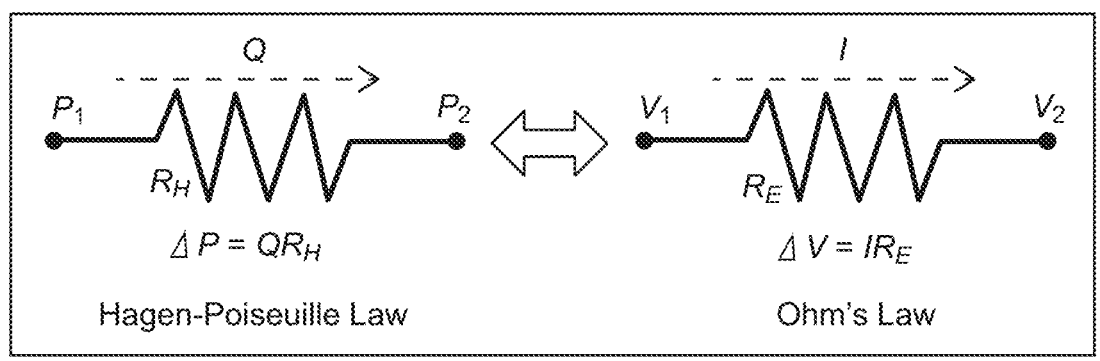
FIG. 1 shows characterization of microfluidic circuits and electrical circuits in accordance with various embodiments.
Figure 2G:
Figure 2G:
Figure 2G:
Figure 2G:
Figure 2G:
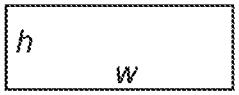
Figure 2G:
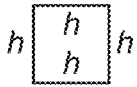

Conventionally, during analysis, the fluid sample is positioned by a mechanical process over the micro-environment sensor structure for a predetermined amount of time to dissolve a reagent and substrate into the sample, and perform the quantitative detection. The mechanical process typically includes the control of a pump to push the fluid sample over the micro-environment sensor structure. However, the microfluidics in conventional test cartridge devices may tend to allow for sample drift over the sensors (the sample continues to flow and move off of the micro-environment sensor structure). The sample drift can be better understood by comparing the microfluidics of conventional test cartridge devices to electrical circuitry. As shown in FIG. 1, pressure-driven laminar, viscous and incompressible flows in microfluidic circuits may be characterized by pressure drop ($\Delta P$), flow rate (Q), and hydraulic resistance ($R_H$), which may be analogous to voltage drop ($\Delta V$), current (I), and electrical resistance ($R_E$), in electrical circuits. More specifically, hydraulic resistance ($R_H$) and electrical resistance ($R_E$) may be comparable, as shown in FIGS. 2A-2G. Hydraulic resistance ($R_H$) depends on viscosity $\eta$ and a geometric factor ($C_{GEO}$), which depends on a cross-sectional shape and area of the channel, as shown in FIGS. 2A-2C; whereas electrical resistance ($R_E$) depends on resistivity ($\rho_E$), as shown in FIGS. 2D-2F.

Furthermore, series and parallel hydraulic resistor elements in microfluidic circuits may be modeled as series and parallel resistors in electrical circuits. FIGS. 3A and 3B show equivalent hydraulic resistances ($R_{HEQ}$) for n resistive elements connected in series and parallel. Kirchoff's current and voltage rules for resistors may be applicable to the resistive elements in microfluidic circuits. For example, the sum of the flow rate (Q) of flows, which may be analogous with current (I), into a node N should equal the sum of the flow rate (Q) of flows leaving the node N. Moreover, the compression of non-rigid materials and/or bubbles within microfluidic channels allow absorption of fluid volume and energy storage. This may be described as hydraulic capacitance ($C_H$), which may be analogous to electrical capacitance (C). Consequently, flows into a hydraulic capacitor may be approximated by: $\Delta Q_H = C_H (\Delta P/dt)$.

Application of these assumptions and analogies between microfluidic circuits of conventional test cartridge devices and electrical circuits are demonstrated in FIGS. 4A, 4B, and 4C. FIG. 4A shows a test cartridge device comprising a single sensor channel having a micro-environment sensor structure. FIG. 4B shows the typical fluidic circuit elements of the test cartridge device including: (i) $R_{WELL}$, which is the combined or series hydraulic resistance of a sample well and channel(s)/features(s) leading to one or more sensors, (ii) $R_S$, which is the hydraulic resistance of the single sensor channel above the one or more sensors, (iii) $R_{PS}$, which is the hydraulic resistance of a small channel after the one or more sensors, (iv) $P_{SAMPLE}$, which is the pressure generated during sample push by a pump, and (v) $P_{ATM}$, which is the atmospheric pressure. These fluidic circuit elements can be modeled in the fluidic circuit shown in FIG. 4C, which includes a series of hydraulic resistor elements whose equivalent resistance may be expressed as: $R_{HEQ} = R_{WELL} + R_S + R_{PS}$.

Figure 5A:
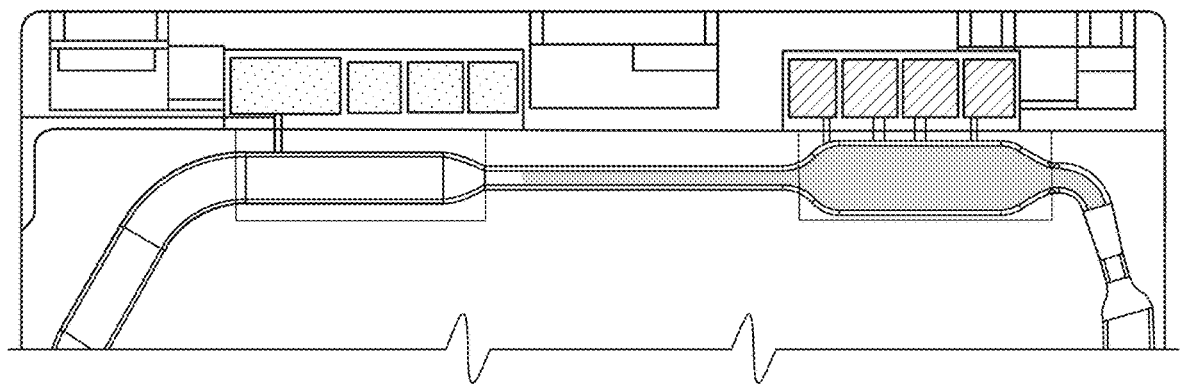
FIGS. 5A, 5B, and 5C show sample drift in a conventional test cartridge device.
Figure 5B:
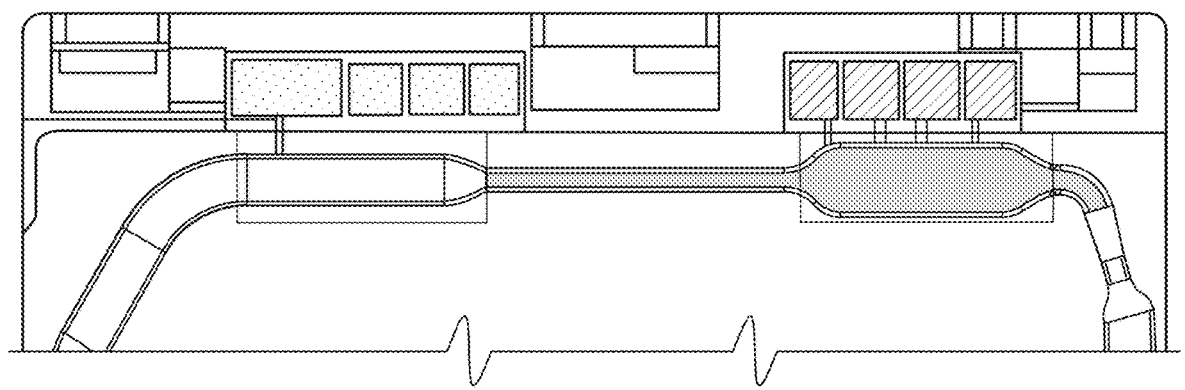
Figure 5C:
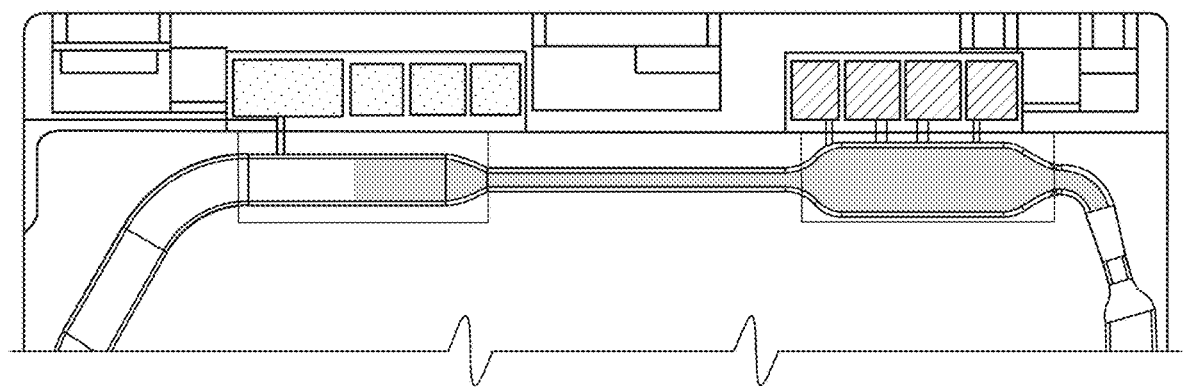

To start the assay, the air bladder is compressed to create pressure ($P_{SAMPLE}$). $P_{SAMPLE}$ is sufficient to overcome $R_{WELL}$ and $R_S$. Sample is now present above the one or more sensors, as shown in FIG. 5A. The analyzer stops generating $P_{SAMPLE}$ once conductivity data from conductometric sensors around the micro-environment sensor structure indicate the one or more sensors are covered with sample. However, the sample continues to flow (i.e., sample drift, which is shown in FIGS. 5B and 5C). The sample drift is thought, without being bound by theory, to be the result of channel dimensions after the one or more sensors being too large ($R_{PS}$) and compliance of cartridge components (e.g., the elastic deformation of components and the change in volume of air). The channel dimensions after the one or more sensors are typically fabricated with the smallest dimensions presently attainable for microfluidics, and thus $R_{PS}$ may not be easily modified to mitigate the sample drift. The compliance exists after pump actuation has stopped due to: (i) the compressibility of air, and (ii) relaxation of carrier-material that serves as the air diaphragm of the pump. However, both the compressibility of air and the elastic deformation of the air diaphragm may not be easily modified to mitigate the sample drift. Accordingly, a new technique is needed to mitigate the sample drift and improve performance for test cartridge devices that utilize micro-environment sensor structures.

To address these problems and provide improved test cartridge devices, a test cartridge device is provided comprising a fluid sample entry port and holding chamber connected to a bifurcation junction of a first channel (a sensor channel) and a second channel (a bypass channel). The first channel comprises an upstream region and a downstream region, and a sensor (e.g., a micro-environment sensor) in the upstream region, a cross-sectional area of the upstream region of the first channel is larger than a cross-sectional area of the downstream region of the first channel, the second channel has a cross-sectional area less than the cross-sectional area of the upstream region of the first channel, and the second channel has a cross-sectional area greater than the cross-sectional area of the downstream region of the first channel. In some embodiments, the first channel and the second channel are connected at a recombination junction to a third channel comprising a vent. In other embodiments, the first channel terminates at a first terminal end and comprises a first vent, for example a first vent at the first terminal end and the second channel terminates at a second terminal end and comprises a second vent, for example, a second vent at the second terminal end. As discussed in detail herein, the second channel (the bypass channel) performs as an additional resistive element that acts as a preferred flow path to relieve excess pressure when the sample reaches the downstream region of the first channel ($R_{PS}$). The relief of the excess pressure when the fluid sample reaches the cross-sectional area of the downstream region of the first channel ($R_{PS}$) acts to mitigate the sample drift and allows for the fluid sample to sit over the sensor long enough to complete the testing analysis. Advantageously, the analogy between fluid circuits and electrical circuits helped to better understand the sample drift problem and guide the design of the bypass channel.

As used herein, the term "micro-environment sensor" refers to a sensor configured such that any reaction occurring in the immediate vicinity of the sensor in a manner sufficient to achieve the desired signal at the sensor will not detectably interfere with (or impact) another reaction occurring at an adjacent sensor during normal usage. The micro-environment sensor structures comprise one or more reagents and one or more substrates in any of a number of different arrangements such that the introduction of the fluid sample, (e.g., whole blood), to the one or more reagents and the one or more substrates is localized to the one or more micro-environment sensors. In particular, the micro-environment sensor structures are configured to physically separate the one or more reagents and/or reaction products from one another to avoid cross-activation or other cross-sensor interference once the one or more reagents have become exposed to the fluid sample.

While the use of a bypass channel as a solution to the aforementioned sample drift problem is described at some length and with some particularity with respect to a specific design and/or performance need for test cartridge devices with microenvironment sensors, it is not intended that the solution be limited to any such particular design and/or performance need. Instead, it should be understood the bypass channel described herein in exemplary embodiments, could also be used in test cartridge devices that utilize other types of sensors such as optical sensors, electrochemical sensors without a microenvironment structure, and combinations of optical and electrochemical sensors. Various contemplated sensors are disclosed in U.S. Pat. Nos. 6,379,883, 5,200,051, and 5,514,253, which are incorporated herein by reference in their entireties. For example, the proposed solution may be of particular usefulness for test cartridge devices that have an optical sensor and a requirement for the sample to sit over the optical sensor for a predetermined amount of time during the acquisition of optical data.

Electrochemical System

Electrochemical detection involves the use of a working electrode (e.g., an amperometric electrode) and a reference electrode (e.g., a counter reference electrode), whereby a constant potential is applied to the working electrode leading to an oxidation-reduction (redox) reaction that can be quantified as a recordable electric current. Electrochemical sensors have found widespread use in the development of point-of-care (POC) and self-test devices, as exemplified by the development of glucose test strips, as they are simple to interface with electronic instruments and reduce device costs. Devices, such as the i-STAT® system (see, e.g., U.S. Pat. No. 7,977,106, the entirety of which is incorporated herein by reference), have employed electrogenic substrates that result in the formation of an electrochemically detectable cleavage product that is proportional to thrombin activity. These devices are then configured to return a clotting time based on a measure of thrombin activity to allow comparisons with standard clotting. Accordingly, in some embodiments, the electrochemical detection system is termed "electrogenic" because the electrochemically detectable species are generated to allow determination of a rate measurement or a test endpoint, (e.g., a diagnostic clotting time). This is similar to the chromogenic or fluorogenic endpoint tests in which a change in the light absorbing or emitting properties of a sample indicates the rate measurement or endpoint, (e.g., a diagnostic clotting time).

Figure 6:
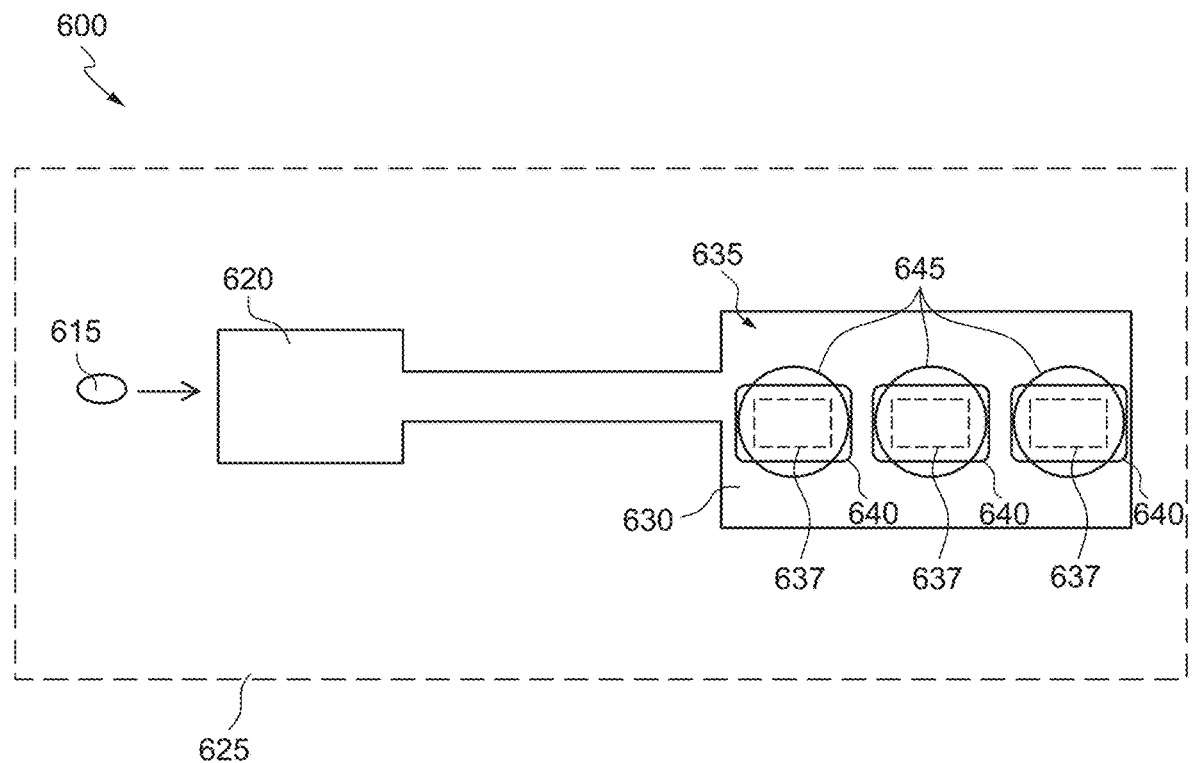
FIG. 6 shows a cartridge schematic in accordance with various embodiments.

FIG. 6 illustrates the principle of an electrochemical detection system 600 (e.g., an amperometric electrochemical detection system) according to some embodiments of the present invention for determination of diagnostic clotting times. However, it should be understood that while specific embodiments are described herein for diagnostic clotting time assays (e.g., prothrombin time (PT), activated partial thromboplastin time (aPTT), and activated clotting time (ACT) assays), the micro-environment sensor structures described herein may also be useful for detecting various analytes of potential interest. More specifically, the electrochemical detection system of the present invention is not limited to the assay of coagulation enzymes. For example, any assay where an enzyme cleaves a substrate molecule to yield an electroactive moiety can use the present methodology. As should be understood, assays can be devised for a variety of other known enzymes in the art, such as for example, glucose oxidase, lactate oxidase, and other oxidoreductases, dehydrogenase based enzymes, and alkaline phosphatase and other phosphatases, and serine proteases without departing from the scope of the present invention. For example, some aspects of the present invention may include a phosphatase assay where ferrocene with a phosphate moiety is present in a micro-environment sensor layer.

The enzyme phosphatase present in a sample may permeate the micro-environment sensor and cleave the phosphate groups enabling the liberated ferrocene molecules to be oxidized at the electrode. Accordingly, the measured current may be a function of the rate of the cleavage reaction, and thus, proportional to the phosphatase activity in the sample.

In an exemplary analysis, a fluidic sample 615, (e.g., whole blood), may be introduced into a sample holding chamber 620 of a cartridge 625 of the present invention. Thereafter, the fluidic sample 615 may be introduced to an analysis region 630 of the cartridge, (e.g., a sensor region) or one or more locations within one or more channels of the cartridge that includes one or more sensors for coagulation detection and optionally for detection of a target analyte (e.g., thrombin activity for a prothrombin time and troponin I). The analysis region 630 includes one or more micro-environment sensors 635 comprising one or more electrodes or transducers 637, one or more reagents 640, and one or more substrates 645 in any number of different possible arrangements. The form and orientation of the electrodes, reagents, and substrate may vary widely depending on the embodiment of the invention, which are described in detail hereafter.

In accordance with some aspects of the invention, the one or more reagents 640 may include a material for inducing coagulation via the intrinsic or extrinsic pathway. Materials suitable for inducing the extrinsic pathway (e.g., PT analysis) may include one or more components selected from the group consisting of non-recombinant tissue factor, recombinant tissue factor, a synthetic or natural lipid, a synthetic or natural phospholipid, a combination of synthetic or natural lipids, and a combination of synthetic or natural phospholipids. In some embodiments a variety of other components may be included within the one or more reagents 640 to contribute to stabilization and deposition/dissolution characteristics of the one or more reagents 640. For example, the one or more reagents 640 may further comprise one or more components selected from the group consisting of carrier proteins such as bovine serum albumin (BSA), stabilizing agents, antimicrobial agents, a calcium salt, a potassium salt, a water soluble polymer, a sugar, gelatin, agarose, a polysaccharide, a saccharide, sucrose, polyethylene glycol, sodium phosphate, glycine, an amino acid, antioxidants, a detergent, a buffer salt, and a buffer such as 4-(2-hydroxyethyl)-1-piperazineethanesulfonic acid (HEPES) buffer.

In accordance with different aspects of the present invention, the one or more reagents 640 may include material suitable for inducing the intrinsic pathway. Materials suitable for inducing the intrinsic pathway (e.g., the aPTT or ACT analysis) may include one or more components selected from ellagic acid, celite, kaolin, diatomaceous earth, clay, silicon dioxide, synthetic or natural lipids, and synthetic or natural phospholipids. In some embodiments a variety of other components may be included within the one or more reagents 640 to contribute to stabilization and/or deposition/dissolution characteristics of the one or more reagents 640. For example, the one or more reagents 640 may further comprise one or more components selected from the group consisting of dextran, dextrin, tergitol, buffers, a carrier protein, an amino acid, stabilizers, antimicrobials, antioxidants, a detergent, a saccharide, a polysaccharide, sucrose, polyethylene glycol, derivatives of polyethylene glycol, glycine, gelatin, buffer such as 4-(2-hydroxyethyl)-1-piperazineethanesulfonic acid (HEPES) buffer, rhamnose, trehalose, and sugars.

In accordance with some aspects of the present invention, the one or more substrates 645 used in the electrogenic assay may have an amide linkage that mimics the thrombin-cleaved amide linkage in fibrinogen. Specifically, the one or more substrates 645 may comprise one or more thrombin-cleavable peptides such as those selected from the group consisting of H-D-Phe-Pip-Arg, H-D-Chg-Abu-Arg, CBZ-Gly-Pro-Arg, Boc-Val-Pro-Arg, H-D-Phe-Pro-Arg, Cyclohexylglycine-Ala-Arg, Tos-Gly-Pro-Arg, Bz-Phe-Val-Arg, Boc-Val-Pro-Arg, Ac-Val-Pro-Arg, Ac-Val-Hyp-Arg, Ac-(8-amino-3,6,dioxaoctanoyl-Val-Pro-Arg, Ac-Gly-Pro-Arg, Ac-(8-amino-3,6,dioxaoctanoyl-Gly-Pro-Arg, Ac-Gly-Hyp-Arg and H-D-Chg-Abu-Arg. Thrombin typically cleaves the amide bond at the carboxy-terminus of the arginine residue because the bond structurally resembles the thrombin-cleaved amide linkage in fibrinogen. The product of the thrombin-substrate reaction includes electrochemically inert compounds such as Tos-Gly-Pro-Arg, H-D-Phe-Pip-Arg, and/or Bz-Phe-Val-Arg- and electroactive compounds or detectable moieties, preferably selected from the group consisting of p-aminophenol, a quinone, a ferrocene, ferrocyanide derivative, other organometallic species, p-nitroaniline, o-dianisidine, 4,4'-bensidine, 4-methoxy-2-naphthylamine, N-phenyl-p-phenylenediamine, N-[p-methoxyphenyl-]-p-phenylenediamine, and phenazine derivatives. The tripeptide sequence was chosen because it renders the substrate virtually non-reactive with blood proteases other than thrombin and the reactivity of thrombin with the arginine amide linkage in the molecule is very similar to its reactivity with the target amide linkage in fibrinogen. When the one or more substrates 645 are present in a blood or blood derivative fluid sample or biological sample, generated active thrombin from activation of the coagulation pathway(s) via the one or more reagents 640 simultaneously converts the one or more substrates 645 and fibrinogen to their cleavage products. The electrochemical species reaction product is detected by the one or more transducers 637, (e.g., an electrochemical transducer).

Micro-Environment Sensor Structures

Figure 7:
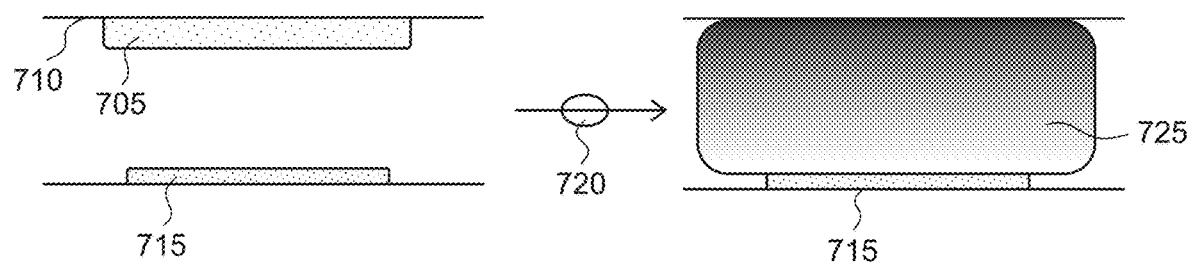
FIGS. 7 and 8 show a channel comprising a dissolvable reagent/substrate and transducer in accordance with various embodiments.

As shown in FIG. 7, traditional POC coagulation assays have employed the reagent/substrate 705 printed as a dry substance on a wall 710 (e.g., a cover) of a channel that is opposite a surface of a sensor 715. The fluid sample 720 would need to be mixed with the dry substance, (e.g., by pump oscillation), to dissolve the reagent/substrate 705 into the fluid sample 720 and generate a mixture 725, which may be in the form of a gradient from a top of the channel down to the sensor 715. However, such a configuration has at least three issues or disadvantages. Firstly, only a small portion of the electroactive product generated via mixture 725 will reach the surface of the sensor 715 and be oxidized, and thus a majority of the electroactive product will not be utilized. As a result, the usage of the reagent/substrate 705 is not efficient. Further, the fluid sample 720 is adulterated with the reagent/substrate 705, which may be undesirable due to its possible impact with other sensors that may come in contact with the fluid sample 720 (e.g., cross-sensor interference). Secondly, in order to achieve adequate analytical precision, the reagent/substrate 705 should be dispersed uniformly in the fluid sample 720 as rapidly as possible. This may be a challenge for point-of-care devices where space and efficiency of mixing can be limited. It is especially true when the reagent/substrate 705 is in solid form and in a very small space relative to a volume of the fluid sample 720. Thirdly, there is a possibility that the substrate interferes with the reagent and/or coagulation factors. For example, mixing the substrate along with the reagent into the sample 720 before the coagulation cascade has been initiated may manifest such interference.

Figure 8:
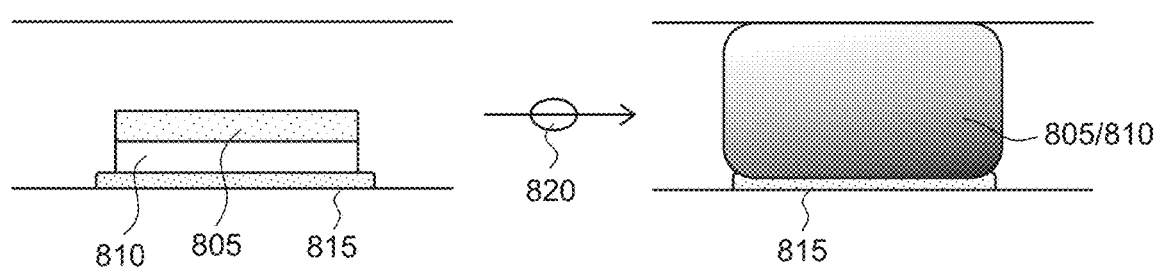

In contrast to the traditional POC coagulation assays, some embodiments, as shown in FIG. 8, present the reagent 805 associated with a substrate layer 810 formed in a localized manner near the surface of the sensor 815. As used herein, the term "substrate" refers to either a molecule which is the target of an enzymatic reaction or a physical entity which forms the foundation of a structure. For example, as shown in FIG. 8, the reagent 805 and the substrate 810 may be printed as a dry substance directly on a surface of the sensor 815. The fluid sample 820 may react with the reagent 805 and the substrate 810 without mixing (e.g., via passive diffusion) (although some degree of mixing, e.g., fluid oscillation, may be desired), in a localized manner creating a gradient from the sensor 815 to a top of the channel. Advantageously, this arrangement of the reagent and the substrate presented directly on a surface of the sensor allows for a majority of the electroactive product to be oxidized, and thus utilized at the surface of the sensor. This sensor arrangement is also beneficial due to the smaller sample volume required in the immediate sensor environment, and thus yielding a more concentrated reagent-to-sample assay zone.

Nonetheless, some of the issues (e.g., mitigation of cross-sensor interference and substrate interference) apparent within the traditional POC coagulation assays may not be overcome by the arrangement shown in FIG. 8. For example, any reaction occurring in the immediate vicinity of the sensor could potentially interfere with the reagent and/or coagulation factors and/or possibly with another reaction occurring at an adjacent sensor (i.e., a sensor within the same channel and within approximately 3 mm of the sensor shown in FIG. 8). As such, this type of sensor arrangement would not be characterized as a micro-environment sensor. However, immobilizing the substrate on the sensor to create a micro-environment sensor has been unexpectedly demonstrated to address many or all of the above-mentioned issues. In accordance with these aspects, the immobilization may be realized by crosslinking (e.g., ultra-violet light, glutaraldehyde, etc.), entrapment, covalent binding, etc. As used herein, the term "immobilized" refers to an aspect of the micro-environment sensor which is substantially limited in movement, and thus localizing this aspect of the micro-environment to a general area.

Figure 9:
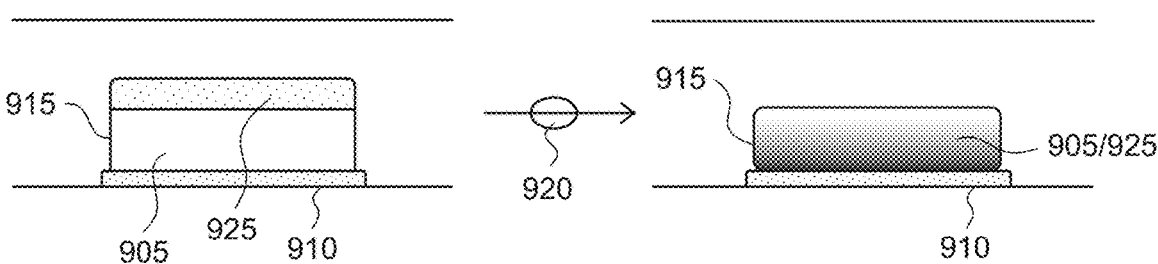
FIG. 9 shows a diffusible reagent, immobilized substrate-polymer layer, and transducer in accordance with various embodiments.

One example of such a micro-environment arrangement is shown in FIG. 9 where the substrate 905 is immobilized on the surface of the sensor 910 using a polymer layer 915. In some embodiments, the immobilization may be performed by coating the sensor 910 with a polymer layer 915 that includes the substrate 905 such that the substrate 905 is immobilized via the polymer layer 915 on the surface of the sensor 910. In other words, the substrate 905 is formed as an immobilized porous substrate-polymer layer on the surface of the sensor 910 to create a vessel for maintaining the reaction of the fluid sample 920, the reagent 925, and the substrate 905 in a localized manner on a surface of the sensor 910. The fluid sample 920 may react with the reagent 925 and the substrate 905 without mixing (although some degree of mixing, e.g., fluid oscillation, may be desired) in a localized manner within the confines of (or above, and then diffused into) the polymer layer 915 formed on the sensor 910.

Advantageously, this arrangement of the immobilized substrate presented directly on a surface of the sensor allows for a majority of the electroactive product to be oxidized, and thus utilized at the surface of the sensor. Even more advantageously, this arrangement of the immobilized substrate provides for a micro-environment capable of maintaining the substrate and the electroactive product in the immediate vicinity of the sensor, and thus mitigating cross-sensor interference with an adjacent sensor during normal usage. Other potential benefits of immobilizing the substrate on the sensor include mitigation of substrate interference via separation of the substrate from the reagent, reduction of material use, simplification of hardware and sensor design, and improvement of product robustness.

Figure 10A:
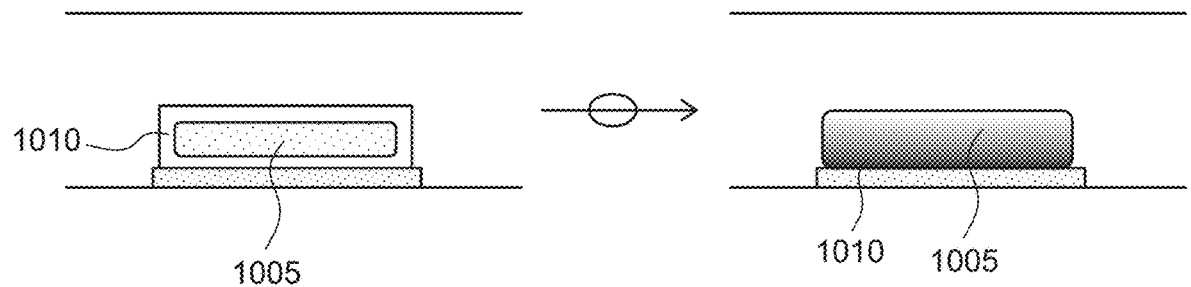
FIGS. 10A, 10B, and 10C illustrate the principle of operation of the microenvironment sensor comprising a reagent and/or substrate, immobilized or not in a polymer layer, and transducer in accordance with various embodiments.
Figure 10B:
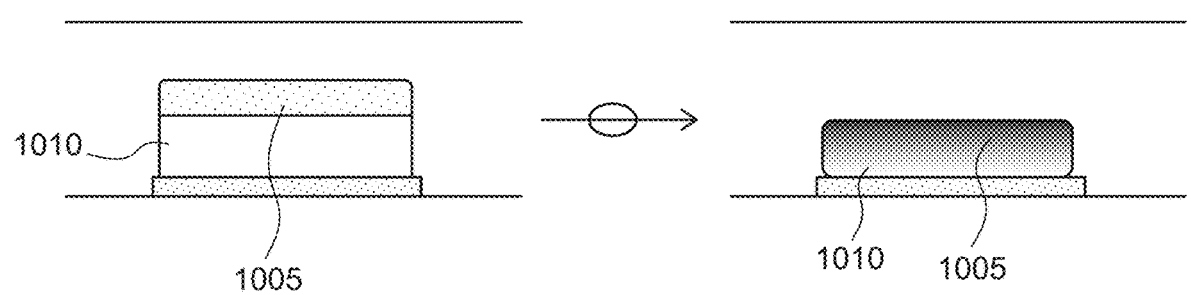
Figure 10C:
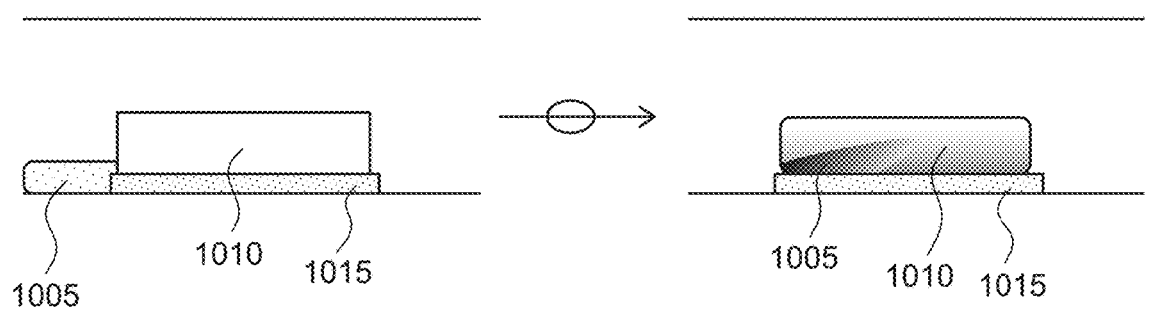

As shown in FIGS. 10A, 10B, and 10C, the micro-environment sensors may have the reagent 1005 and the immobilized substrate-polymer layer 1010 positioned in a number of different arrangements with the components interacting with each other without mixing, although some degree of oscillation may be desired. For example, as shown in FIG. 10A, the reagent 1005 may be positioned within or encapsulated by the immobilized substrate-polymer layer 1010 (e.g., the reagent is integrated within the immobilized substrate-polymer layer). As shown in FIG. 10B, the reagent 1005 may be coated over the immobilized substrate-polymer layer 1010 (e.g., the reagent is a separate layer dispensed on top of the immobilized substrate-polymer layer). As shown in FIG. 10C, the reagent 1005 may be positioned substantially adjacent to the immobilized substrate-polymer layer 1010 and at least one transducer of the sensor 1015 (e.g., the reagent is positioned within the channel such that the reagent is abutted to or within an interactive distance of the substrate-polymer layer and/or the at least one transducer so as to still function in conjunction with each other). As used herein, an interactive distance means less than a longest dimension of the sensor with the constraint of the reagent being positioned within a same plane or on a same wall/surface of a channel as the sensor. Other variants will also be apparent to those skilled in the art without departing from the spirit and scope of the present invention, for example the reagent 1005 may be formed as a combination of that shown in FIGS. 10B and 10C, or as shown in FIG. 10C with only part of the reagent 1005 shown in FIG. 10B.

Figure 11:
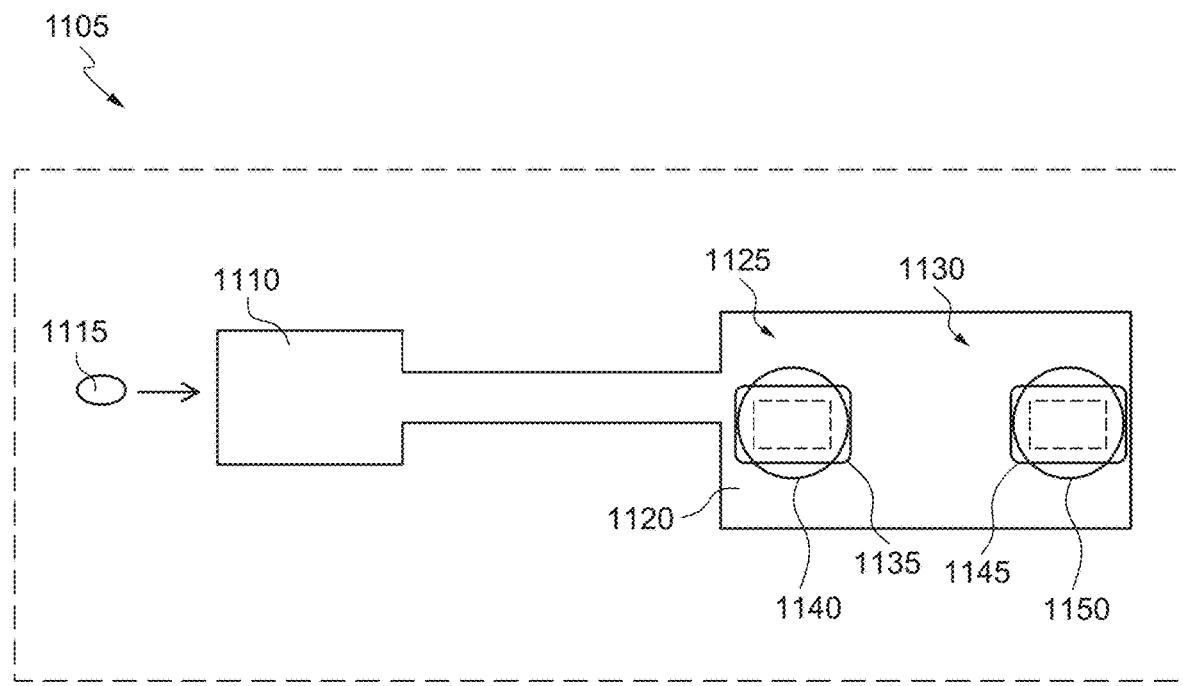
FIG. 11 shows a cartridge schematic in accordance with various embodiments.

As shown in FIG. 11, in some embodiments, an analysis cartridge 1105 is provided comprising an inlet chamber 1110 configured to receive a fluid sample 1115 and a channel 1120 fluidically connected to the inlet chamber 1110 and configured to receive the fluid sample 1115 from the inlet chamber 1110. The channel 1120 may comprise an array of micro-environment sensors, e.g., a first micro-environment sensor 1125 and a second micro-environment sensor 1130. The first micro-environment sensor 1125 may comprise a first reagent 1135 and a first substrate 1140 (e.g., a substrate immobilized within a polymer layer) configured to detect a first diagnostic clotting time. For example, the first micro-environment sensor 1125 may be a PT sensor comprising a first reagent 1135 that includes one or more components, as discussed herein, specific for triggering the extrinsic coagulation pathway and a first substrate layer 1140 comprising a thrombin-cleavable peptide with a detectable moiety as discussed herein. The second micro-environment sensor 1130 may comprise a second reagent 1145 and a second substrate 1150 (e.g., a substrate immobilized within a polymer layer) configured to detect a second diagnostic clotting time. For example, the second micro-environment sensor 1130 may be an aPTT sensor comprising a second reagent 1145 that includes one or more components, as discussed herein, specific for triggering the intrinsic coagulation pathway and a second substrate layer 1150 comprising a thrombin-cleavable peptide with a detectable moiety (e.g., a reagent and a substrate immobilized within a polymer layer). As should be understood, although the above-described analysis cartridge 1105 is discussed with respect to a PT sensor and an aPTT sensor, various combinations and numbers of sensors, (e.g., a PT sensor, an aPTT sensor, and an ACT sensor), are contemplated by the present invention without departing from the scope of the present invention. For example, the first micro-environment sensor 1125 may be a PT sensor, and the second micro-environment sensor 1130 may be an aPTT sensor or an ACT sensor. In another aspect, the first micro-environment sensor 1125 is an aPTT sensor, and the second micro-environment sensor 1130 is a PT sensor or an ACT sensor. In another aspect, the first micro-environment sensor 1125 is an ACT sensor, and the second micro-environment sensor 1130 may be an aPTT sensor or a PT sensor. In still other embodiments, one of the micro-environment sensors is a PT sensor, an aPTT sensor, or an ACT sensor, and another of the sensors is a sensor for detecting an analyte, related or unrelated to coagulation. In yet other embodiments, one of the micro-environment sensors is a sensor for detecting an analyte, unrelated to coagulation, and another of the sensors is a sensor for detecting an analyte, related or unrelated to coagulation.

Advantageously, the micro-environment sensor structures of the present invention are configured to physically separate the one or more reagents and substrates to avoid cross-activation and/or interference of the cascade pathways once the one or more reagents and substrates have become exposed to the fluid sample. Even more advantageously, incorporation of the immobilized substrate and/or reagent polymer layer into the coagulation assays provides for the ability to perform the coagulation assays without requiring or while minimizing mixing, (e.g., oscillation of the fluid sample in a channel), because coagulation activation occurs in a localized and concentrated area over the sensor with subsequent propagation of the test reaction into the immobilized layer, ultimately resulting in oxidation at the transducer.

Immobilized Substrate-Polymer Layer

Figure 12:
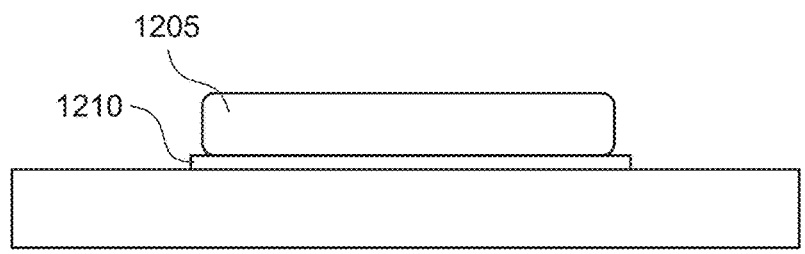
FIG. 12 shows a side view of the fabrication of an immobilized reagent/substrate-polymer layer in accordance with various embodiments.

In various embodiments, in order to physically separate the one or more assays from one another to avoid cross-activation and promote localization of electrochemical or optical signals over the transducers, an immobilized substrate and/or reagent-polymer layer may be selectively patterned onto the sensors (e.g., coated over the transducer or working electrode/optical detector). As shown in FIG. 12, the immobilized polymer layer 1205 may be formed by either spin coating or by microdispensing. More specifically, an aqueous polymer matrix comprising one or more reagents and substrates and a polymer, such as a photoformable polymer (e.g., polyvinylalcohol (PVA)), may be utilized for immobilizing the one or more substrates on or near the transducer 1210. Additives including, but not limited to, a protein such as BSA, a sugar or sugar alcohol, such as sucrose, sorbitol, or mannitol, may also be included in the aqueous matrix. To those skilled in the art of polymer chemistry, the addition of some substances to the polymer layer(s) results in a number of alterations to, including but not limited to, swelling reactions, diffusion coefficients, molecule stability, porosity, transport, reaction kinetics and the like. These alterations can be used to modulate the micro-environment sensor response as required.

In accordance with some aspects of the invention, the one or more substrates may comprise one or more thrombin-cleavable peptides selected from the group consisting of H-D-Phe-Pip-Arg, H-D-Chg-Abu-Arg, CBZ-Gly-Pro-Arg, Boc-Val-Pro-Arg, H-D-Phe-Pro-Arg, Cyclohexylglycine-Ala-Arg, Tos-Gly-Pro-Arg, Bz-Phe-Val-Arg, Boc-Val-Pro-Arg, Ac-Val-Pro-Arg, Ac-Val-Hyp-Arg, Ac-(8-amino-3,6,dioxaoctanoyl-Val-Pro-Arg, Ac-Gly-Pro-Arg, Ac-(8-amino-3,6,dioxaoctanoyl-Gly-Pro-Arg, Ac-Gly-Hyp-Arg and H-D-Chg-Abu-Arg. Optionally the two or more of these substrates may be mixed to obtain the thrombin activities and diffusional properties desired in the immobilized substrate and/or reagent polymer layer.

In accordance with some aspects of the invention, the polymer that contains the substrate may comprise one or more materials, optionally in matrix form. The material for the polymer, for example, may be selected from the group consisting of PVA, styrylpyridinium polyvinylalcohol (SBQ-PVA), agarose, polyacrylamide, polymethyl methacrylate, N-methylpyrrolidone, polyvinylpyrrolidone, polyimide, a film-forming latex, sepharose, polyurethanes, acrylates, methacrylates, polyethylene glycols, polylactic acid, poly(lactic co-glycolic acid), hydroxypropyl cellulose, celluloses, derivatives of cellulose, hydroxypropylmethylcellulose acetate succinate, inulin, fructans, derivatives of fructans, polyglycolic acid, Elvace™, carboxymethyl cellulose, polylactic acid, and poly(lactic co-glycolic acid). In some embodiments in which the material for the polymer comprises celluloses (e.g., hydroxypropyl cellulose), additives such as a plasticizer (e.g., triethyl citrate, acetyl triethyl citrate, propylene glycol, glycerin, trimethylolpropane, polyethylene glycols, fatty acids, and derivatives thereof) and/or crosslinkers (e.g., carboxylic acids, glyoxal, and any resin which is reactive with the available hydroxyl groups of the cellulose) may also be included in the aqueous matrix. Crosslinking of the materials may also affect the polymer layer swelling, permeability, diffusion, reaction kinetics etc. in order to modulate the sensor response as required.

Further to selection of the material for the polymer, another benefit of immobilizing the substrate and/or reagent includes using the immobilizing matrix as a localized interferant neutralizer. For example, the selection of the material for the polymer may be dependent upon the type of diagnostic clotting test to be performed using the immobilized polymer layer. For example, advantageously and unexpectedly it has been found that inclusion of cross-linked or non-cross-linked SBQ-PVA in the immobilized polymer layer imparts a heparin neutralizing property or heparin insensitivity into the immobilized polymer layer. Consequently, in embodiments in which the diagnostic clotting test to be performed using the immobilized polymer layer is a heparin sensitive test (e.g., the PT test is known to be moderately sensitive to clot inhibitors such as heparin), the polymer may be selected to be a heparin-neutralizing polymer such as cross-linked or non-cross-linked SBQ-PVA. In some embodiments, the PVA may be a photo-activated stilbizonium salt.

Figure 13A:
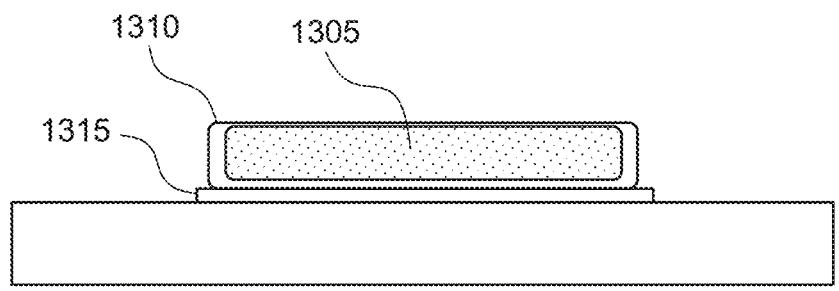
FIGS. 13A, 13B, and 13C show multiple arrangements for a diffusible reagent, immobilized substrate-polymer layer, and transducer in accordance with various embodiments.

In some embodiments, the one or more reagents and substrates 1305 may be immobilized within the polymer layer 1310 as shown in FIG. 13A. In accordance with these aspects, the aqueous substrate-polymer-reagent matrix comprising one or more substrates, a polymer such as photoformable polymer (e.g., PVA), and one or more reagents may be utilized for immobilizing the one or more substrates and the one or more reagents on or near the transducer 1315. The immobilized polymer layer 1310 may be formed by either spin coating or by microdispensing the aqueous substrate-polymer-reagent matrix. In preferred embodiments, the one or more reagents or substrates 1305 for an assay such as an aPTT or ACT test may be immobilized within the polymer layer 1310 and the dried volume of the immobilized reagent-substrate-polymer layer 1310 comprising the one or more reagents or substrates 1305 may be in the range of about 0.55-2.0 nL, preferably in the range of about 1.0-1.5 nL. In some embodiments, the immobilized polymer layer 1310 is substantially planar and has a thickness in the range of about 0.1-100 µm. In additional or alternative embodiments, the immobilized polymer layer 1310 is substantially domed and has a maximum thickness of the dome in the range of about 0.1-100 µm. Although the reagents are shown in FIG. 13A heterogeneously localized in the central region of the polymer layer 1310, in certain embodiments the reagent(s) is/are homogeneously dispersed throughout the substrate-polymer layer.

Figure 13B:
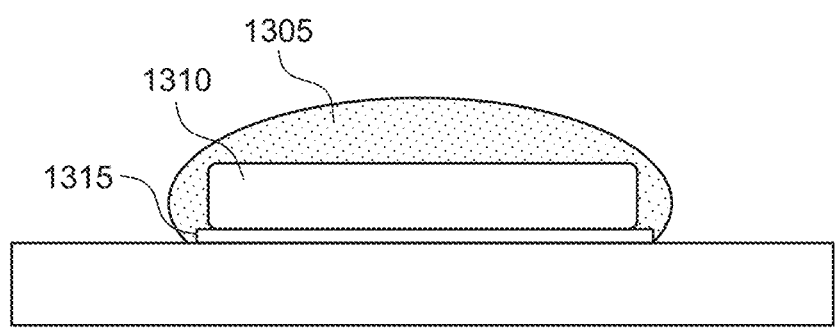
Figure 13C:
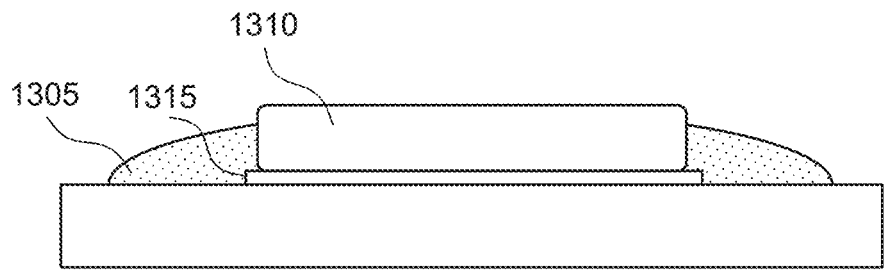

In some embodiments, the one or more reagents or substrates 1305 may be formed as a separate layer over and/or adjacent to the immobilized polymer layer 1310 as shown in FIGS. 13B and 13C. Further, the one or more regents or substrates 1305 may be localized/immobilized together or in separate locations. In accordance with these aspects of the present invention, the one or more reagents or substrates 1305 may be spin coated or printed over and/or adjacent to the immobilized polymer layer 1310 (e.g., the PVA layer) to localize electrochemical or optical signals over or near the transducer 1315. In preferred embodiments, the one or more reagents or substrates 1305 for a PT test may be formed separate from the immobilized polymer layer 1310 and the dried volume of the immobilized polymer layer 1310 may be in the range of 1.5-2.2 nL, preferably in the range of 1.60-2.00 nL. In some embodiments, the immobilized polymer layer 1310 is substantially planar and has a thickness in the range of about 0.1-100 µm. In additional or alternative embodiments, the immobilized polymer layer 1310 is substantially domed and has a maximum thickness of the dome in the range of about 0.1-100 µm.

Sensor and Chip Design

A preferred embodiment of a microfabricated sensor array comprises at least one sensor or transducer (e.g., a working electrode or optical detector). For example, the microfabricated sensor array may comprise a pair of micro-environment sensors or transducers comprising a first micro-environment sensor or transducer (e.g., a PT sensor) and optionally a second micro-environment sensor or transducer (e.g., an aPTT sensor). In some embodiments, the micro-environment sensors or transducers may be fabricated as adjacent structures, respectively, on a silicon chip.

In additional or alternative embodiments, the microfabricated sensor array may further comprise in addition to the first micro-environment sensor or transducer and optionally the second micro-environment sensor or transducer, one or more blood chemistry sensors. For example, the sensor array may further comprise one or more of sensors configured to measure one or more of sodium, potassium, calcium, chloride, carbon dioxide, glucose, blood urea nitrogen (BUN), creatinine, pH, partial pressure $CO_2$, partial pressure $O_2$, lactate, magnesium, or another analyte.

Figure 14:
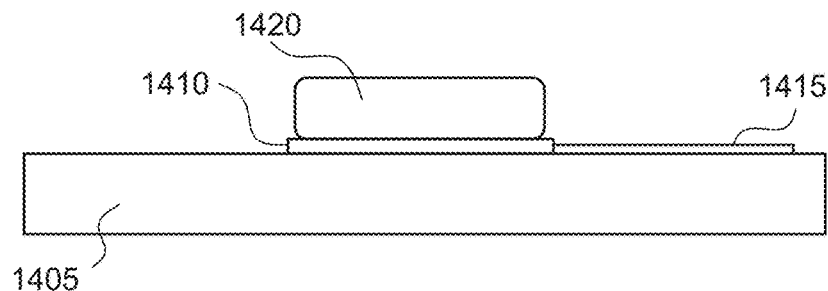
FIG. 14 shows a side view of the fabrication of a sensor in accordance with various embodiments.

In some embodiments, the transducers may be formed as electrodes with gold surfaces coated with a photo defined polyimide layer. For example, wafer-level micro-fabrication of a preferred embodiment of the sensor array may be achieved as shown in FIG. 14. A planar non-conducting substrate 1405 may be used as a base for the sensor array. A conducting layer 1410 may be deposited on the substrate 1405 by conventional means, (e.g., conductive printing), or micro-fabrication technique known to those of skill in the art to form at least one transistor. The conducting layer 1410 may comprise a noble metal such as gold, platinum, silver, palladium, iridium, or alloys thereof, although other unreactive metals such as titanium and tungsten or alloys thereof may also be used, as many non-metallic electrodes of graphite, conductive polymer, or other materials may also be used.

For example, a base electrode may comprise a square array of 5-10 µm gold disks, e.g., 7 µm gold disks, on 15 µm centers. The array may cover a region, (e.g., a circular region), approximately 300 to 900 µm in diameter, optionally 400-800 µm or about 600 µm in diameter, and may be formed by photo-patterning a thin layer of polyimide or photoresist of thickness up to 1.5 µm over a substrate made from a series of layers comprising Si, $SiO_2$, TiW, and/or Au, or combinations thereof. In some embodiments, the base electrode has a working area of about 130,000 to 300,000 sq µm, the volume of sample directly over the sensor may be about 0.1-0.3 µL, and the volume of the sample over the chip may be 1-3 µL. In accordance with these aspects of the present invention, the channel in a region of the base electrode has a volume to sensor area ratio of less than about 64, to about 1 square mm, preferably less than about 50 mm to about 2 square mm, more preferably less than about 100 µm to about 500 square µm. Accordingly, the array of microelectrodes affords high collection efficiency of a detectable moiety that is an electroactive species with a reduced contribution from any electrochemical background current associated with the capacitance of the exposed metal. In particular, openings in the insulating polyimide or photoresist layer define a region of gold electrodes at which the electroactive species, (e.g., p-aminophenol), may be oxidized such as in a two electron per molecule reaction.

Micro-fabrication techniques (e.g. photolithography and plasma deposition) may be utilized for construction of the multilayered sensor structures in confined spaces. For example, methods for micro-fabrication of electrochemical immunosensors on silicon substrates are disclosed in U.S. Pat. No. 5,200,051, which is hereby incorporated by reference in its entirety, and include, for example, dispensing methods, methods for attaching substrates and reagents to surfaces including photoformed layers, and methods for performing electrochemical assays.

The microfabricated sensor array may also comprise an electrical connection 1415 and an immobilized polymer layer 1420 (as discussed above with respect to FIGS. 9, 10A, 10B, 10C, 13A, 13B, and 13C), which is deposited onto at least a portion of the conducting layer 1410 and/or the non-conducting substrate 1405. In the present invention, the immobilized polymer layer 1420 may be a porous polymer layer comprising a thrombin-cleavable peptide with a detectable moiety that is configured to respond to the presence of active thrombin by producing a change that is capable of being measured.

Figure 15:
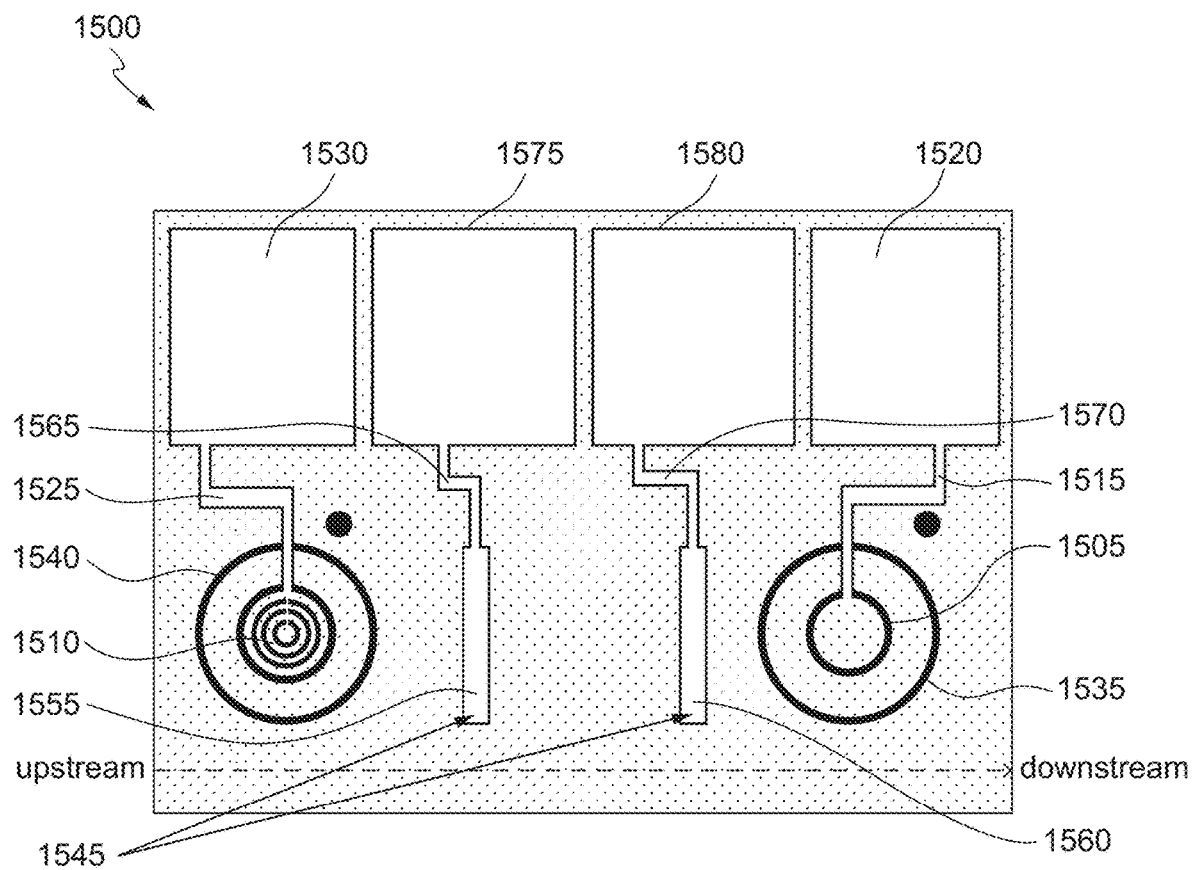
FIGS. 15 and 16 show multiple sensor configurations in accordance with various embodiments.
Figure 16:
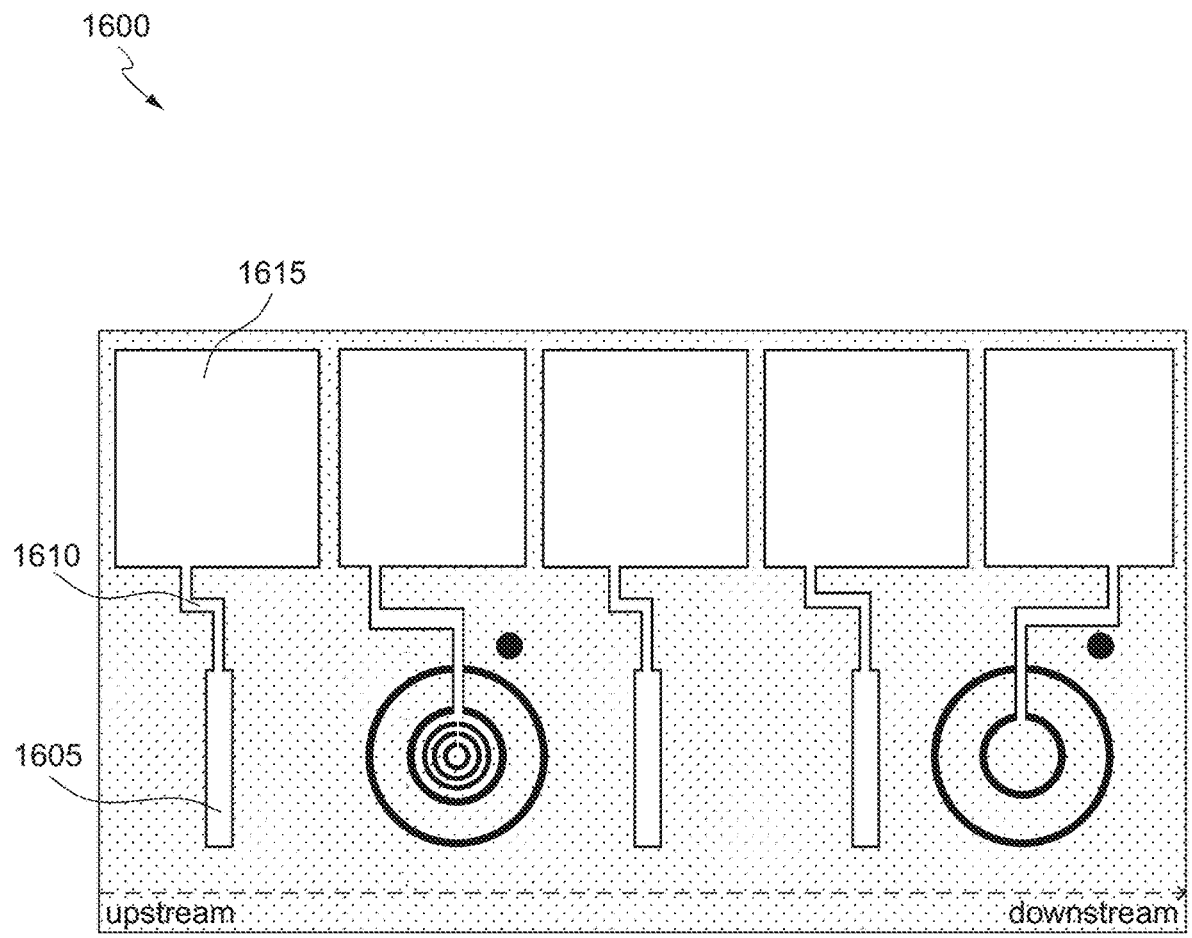

As shown in FIGS. 15 and 16, in some embodiments, the microfabricated sensor array may comprise a silicon chip 1500 that includes micro-environment amperometric sensors or transducers 1505 and 1510 located on the silicon chip 1500. The sensor 1505 may be connected via wiring 1515 to a first amperometric pin 1520 (e.g., temporary electrical connector) and the sensor 1510 may be connected via wiring 1525 to a second amperometric pin 1530 (e.g., temporary electrical connector). In some embodiments, the sensor 1505 may be configured as an aPTT sensor and the sensor 1510 may be configured as a PT sensor both of which are formed on the single silicon chip 1500 and positioned within one or more channels of the point-of-care test cartridge. As illustrated in FIG. 15, the sensor 1505 may be constructed with a target reticle design preferably comprising concentric rings (e.g., 1, 2, 3, 4 or more concentric rings) in a first area of the silicon chip 1500 and the sensor 1510 may be constructed with a target reticle design preferably comprising concentric rings (e.g., 1, 2, 3, 4 or more concentric rings) in a second area of the silicon chip 1500. Specifically, the design and arrangement of the sensors 1505 and 1510 on the chip 1500 are selected based on printing and performance characteristics for each of the sensors 1505 and 1510. However, it should be understood to those of ordinary skill in the art that any design or arrangement for the sensors is contemplated without departing from the spirit and scope of the present invention. Furthermore, although the sensors 1505 and 1510 in the example in FIG. 15 are amperometric sensors, other electrochemical processes or optical processes which use other electrochemical or optical sensors, (e.g., optical wave guides and charge-coupled device (CCD) camera chips), can be used. For example, a potentiometric sensor may be used to detect ion species such as $Na^+$ or $K^+$.

As described herein, the amperometric sensors or transducers 1505 and 1510 may be formed as electrodes with gold surfaces that are exposed (e.g., no polyimide or photoresist covering) to the inside environment of the channel and configured to directly contact a biological sample disposed within the channel. The wirings 1515 and 1525 may be formed with gold surfaces that are coated with a photo defined polyimide or photoresist layer such that the wirings 1515 and 1525 are insulated from exposure to the biological sample disposed within the channel. The wirings 1515 and 1525 may be formed comprising containment ring structures 1535 and 1540 configured to contain the immobilized reagent-substrate-polymer layer. For example, the immobilized reagent-substrate-polymer layer (as discussed above with respect to FIGS. 4, 7A, 7B, and 7C) may be deposited onto at least a portion of the sensors 1505 and/or 1510 within the containment ring structures 1535 and/or 1540. The wirings 1515 and 1525 terminate at the first amperometric pin 1520 and the second amperometric pin 1530 respectively, which are used to make contact with a connector in an analyzer or cartridge reader (e.g., an i-STAT® cartridge reader as described in U.S. Pat. No. 4,954,087, the entirety of which is incorporated herein by reference).

In the preferred embodiments of the present invention, the analyzer applies a potential via the first amperometric pin 1520 and the second amperometric pin 1530 between each of the amperometric sensors 1505 and 1510 and a reference electrode (described in detail below with respect to FIG. 17), and measures current changes generated by a cleaved substrate as an electrochemical signal. The electrochemical signal being proportional to the concentration of the product in the biological sample. The amperometric sensors 1505 and 1510 have an applied potential of approximately +0.4 V versus the reference electrode and, in another preferred embodiment, the amperometric sensors 1505 and 1510 have an applied potential of approximately +0.1 V versus the reference electrode. The signal generated by the enzyme reaction product at approximately +0.1V is distinguishable from the signal generated by the unreacted substrate at approximately +0.4 V.

In the embodiments of the invention which use the thrombin cleavable peptide Tos-Gly-Pro-Arg-, H-D-Phe-Pip-Arg, or Bz-Phe-Val-Arg attached to an N-phenyl-p-phenylenediamine or N-[p-methoxyphenyl-]-p-phenylenediamine detectable moiety, the intact substrates are detected at a voltage of approximately +0.4V. The electrogenic reaction products N-phenyl-p-phenylenediamine or N-[p-methoxyphenyl-]-p-phenylenediamine are detected at a voltage of approximately +0.1V. Thus in these embodiments, the analyzer applies a potential to the amperometric sensors 1505 and 1510 with the generation of an electrochemical signal which is proportional to the concentration of the substrate in the biological sample. Also, the analyzer applies a potential to the amperometric sensors 1505 and 1510 with the generation of an electrochemical signal which is proportional to the concentration of the product in the biological sample. After hydrolysis of the substrate by thrombin, a product is formed which reacts at the amperometric sensors 1505 and 1510 with the generation of a signal distinguishable from the signal generated by the substrate.

It should be noted that the exact voltages used to amperometrically detect the substrate and the product will vary depending on the chemical structure of the substrate and product. It is important that the difference in the voltages used to detect the substrate and the product be great enough to prevent interference between the readings. With some substrates, the voltage required to electrochemically detect the substrate is so high as to be beyond practical measurement in an aqueous buffered solution. In these cases, it is only necessary that the product be detectable amperometrically.

In some embodiments, the silicon chip 1500 shown in FIG. 15 may further include a conductometric sensor 1545 (e.g., hematocrit sensors). The conductimetric sensor 1545 is configured to determine biological sample arrival and/or departure at the amperometric sensors 1505 and 1510. More specifically, the conductometric sensor 1545 lies perpendicular to a length of the channel or sensor channel, and an electrical resistance between pairs of electrodes, for each sensor may be used to monitor a relative position of a fluid front of the biological sample. At the extremes, an open circuit reading indicates that the biological sample has been pushed off the amperometric sensors 1505 and 1510 and a closed circuit reading indicates the amperometric sensors 1505 and 1510 are covered with the biological sample.

As shown in FIG. 15, the conductometric sensor 1545 may comprise at least two electrodes 1555 and 1560 (i.e., first electrode pair) positioned upstream of a midpoint of the amperometric sensor 1505. The electrodes 1555 and 1560 may be connected via wirings 1565 and 1570 to a conductometric low pin 1575 and an AC source or conductometric high pin 1580, respectively (e.g., temporary electrical connectors). The wirings 1565 and 1570 may be formed with a gold surface that is coated with a photo defined polyimide or photoresist layer such that the wirings 1565 and 1570 are insulated from exposure to the biological sample disposed within the channels.

As shown in FIG. 16, in another embodiment, the silicon chip 1600 may further include a third conductometric electrode 1605. The electrode 1605 may be connected via wiring 1610 to a second AC source or conductometric high pin 1615 (e.g., temporary electrical connector). In accordance with these aspects, the use of a third electrode allows for two binary fluid detection events, (e.g., both are OFF/ON), which is easily detectable with the current circuitry and software limitations. In the case of two conductivity electrodes (shown in FIG. 15), the current circuitry and software relies on the ability to detect two 'drops' in the resistance of the sample in quick succession. Typically, the first drop is large as it goes from a dry state to a wet state and the circuit is completed. The second drop in resistance, when the sample arrives over the second amperometric sensor, is much smaller and therefore more difficult to differentiate from signal noise and small changes in the signal. In addition, the amplitude of each resistance change varies depending on the sample properties. Accordingly and advantageously, in some embodiments, the arrangement of having three conductometric electrodes allows for two switchable conductivity paths using the conductometric sensor (shown in FIGS. 15 and 16).

Figure 17:
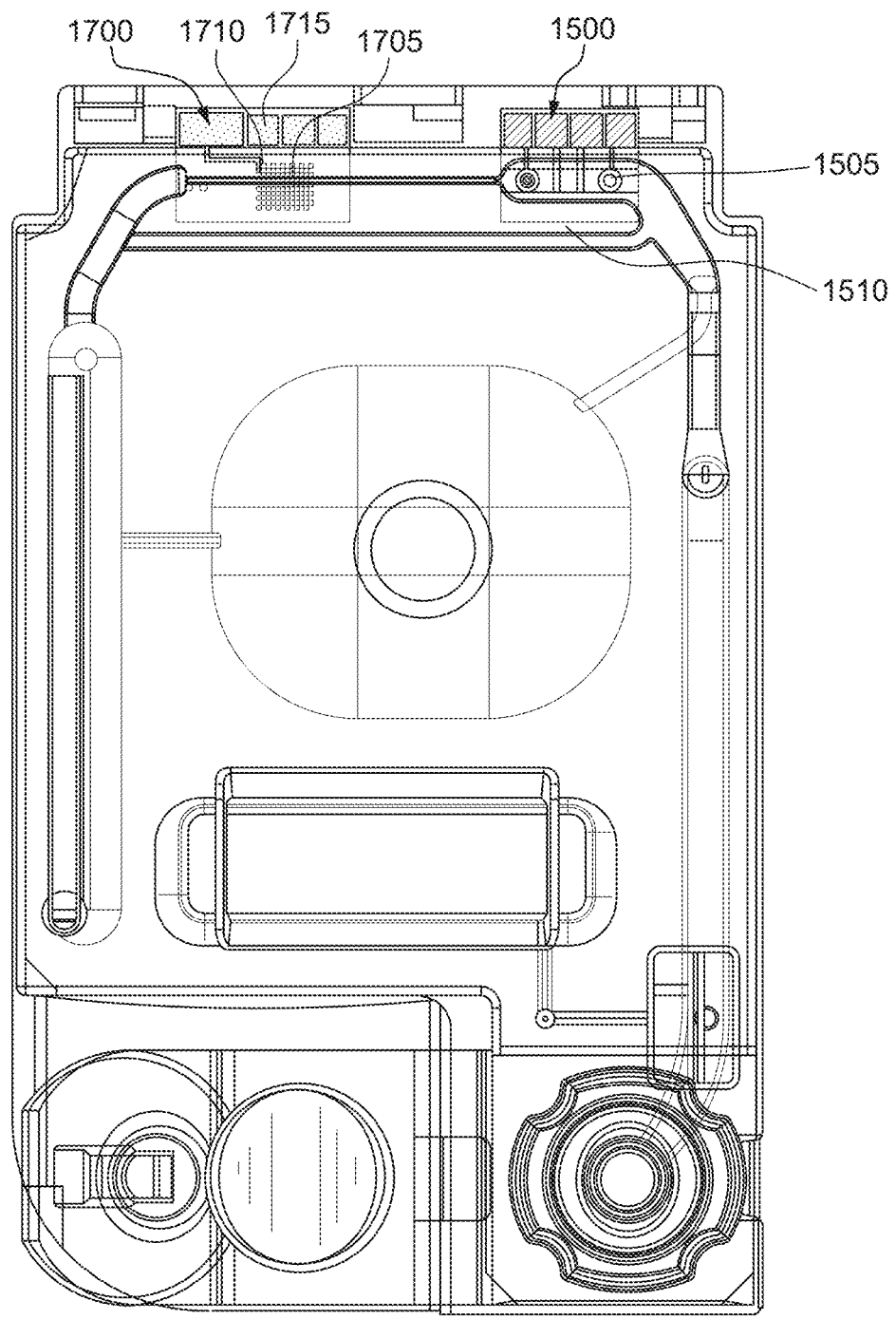
FIG. 17 shows a top view of a disposable sensing device in accordance with various embodiments.

As shown in FIG. 17, in some embodiments, the microfabricated sensor array may further comprise a ground chip 1700 that includes a reference sensor or electrode 1705. In accordance with aspects of the present invention, in which the sensors 1505 and 1510 are amperometric sensors, the reference electrode 1705 may be configured as a counter electrode to complete the circuitry. In a preferred embodiment, the reference electrode 1705 may comprise silver metal (Ag) and its silver salt (AgCl) deposited on a solid substrate (i.e., an Ag/AgCl reference electrode). The reference electrode 1705 may be connected via wiring 1710 to a reference pin 1715 (e.g., temporary electrical connector). The microfabricated sensor array may be designed such that the ground chip 1700 is positioned upstream of the semiconductor chip 1500 as discussed in further detail with respect to FIGS. 15 and 16. However, it should be understood that other arrangements for sensor and ground chips are possible without departing from the spirit and scope of the present invention. For example, the sensor array may further comprise one or more additional sensor chips (not shown) configured to detect various analytes of potential interest, such as troponin I, troponin T, CKMB, procalcitonin, bHCG, HCG, NTproBNP, proBNP, BNP, myoglobin, parathyroid hormone, d-dimer, NGAL, galectin-3, and/or PSA, among other analytes.

Figure 18:
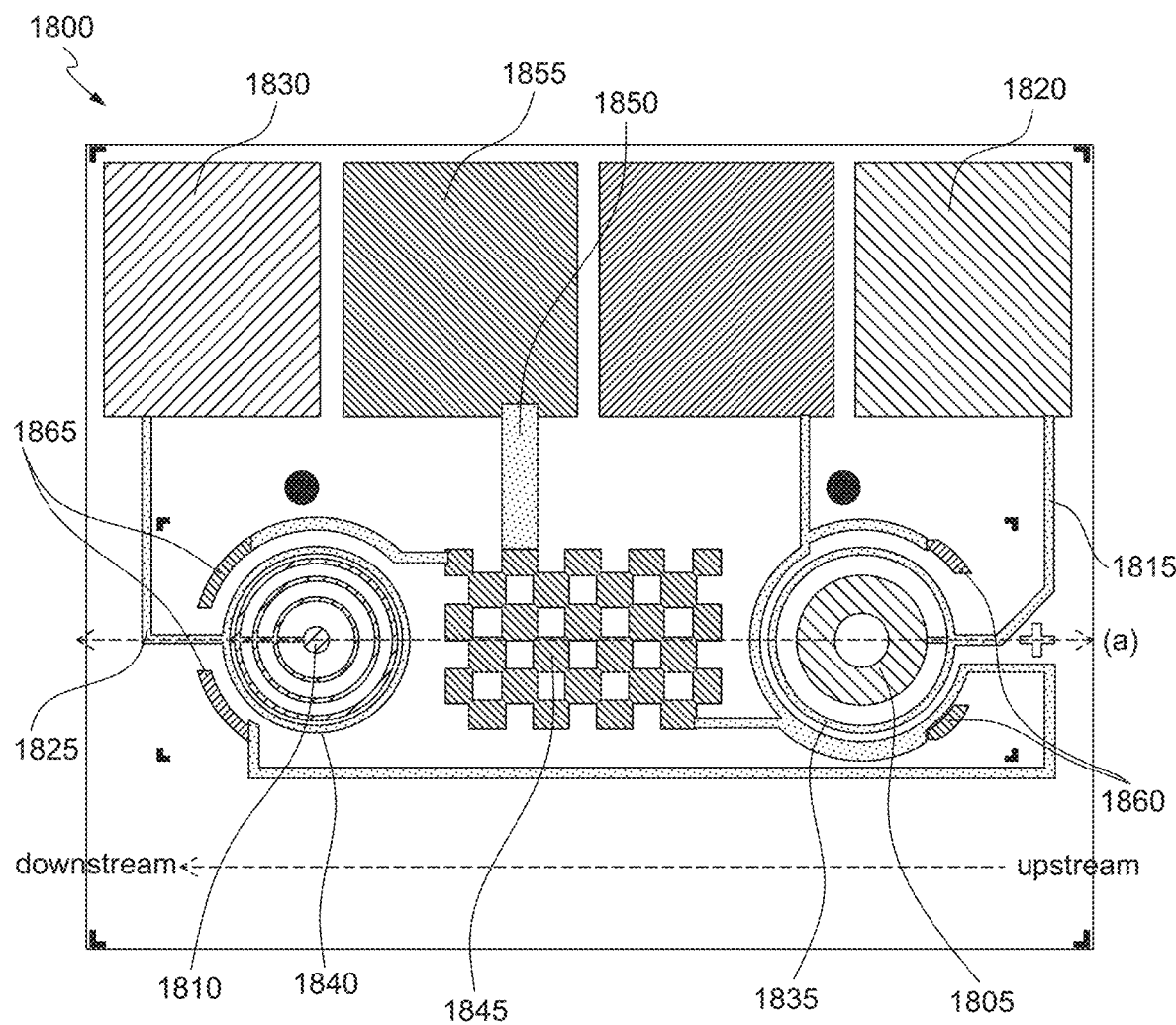
FIGS. 18-20 show multiple sensor configurations in accordance with various embodiments.

As shown in FIG. 18, in preferred embodiments, the microfabricated sensor array may comprise a silicon chip 1800 that includes micro-environment amperometric sensors or transducers 1805 and 1810 located on a same vertical plane (a) of the silicon chip 1800. The sensor 1805 may be connected via wiring 1815 to a first amperometric pin 1820 (e.g., temporary electrical connector) and the sensor 1810 may be connected via wiring 1825 to a second amperometric pin 1830 (e.g., temporary electrical connector). In some embodiments, the sensor 1805 may be configured as an aPTT sensor and the sensor 1810 may be configured as a PT sensor both of which are formed on a single chip 1800 and positioned within the channel of the point-of-care test cartridge. As illustrated in FIG. 18, the sensor 1805 may be constructed with a donut shaped design in an upstream position to that of the sensor 1810 constructed with a target reticle design comprising a plurality of concentric rings (e.g., 2, 3, 4 or more concentric rings). Specifically, the design and arrangement of the sensors 1805 and 1810 on the chip 1800 are selected based on printing and performance characteristics for each of the sensors 1805 and 1810. However, it should be understood to those of ordinary skill in the art that any design or arrangement for the sensors is contemplated without departing from the spirit and scope of the present invention. Furthermore, although the sensors 1805 and 1810 in the example in FIG. 18 are amperometric sensors, other electrochemical processes or optical processes which use other electrochemical or optical sensors can be used. For example, a potentiometric sensor may be used to detect ion species such as $Na^+$ or $K^+$.

As described herein, the sensors or transducers 1805 and 1810 may be formed as electrodes with gold surfaces that are exposed (e.g., no polyimide or photoresist covering) to the inside environment of the channel and configured to directly contact a biological sample disposed within the channel. The wirings 1815 and 1825 may be formed with gold surfaces that are coated with a photo defined polyimide layer such that the wirings 1815 and 1825 are insulated from exposure to the biological sample disposed within the channel. The wirings 1815 and 1825 may be formed comprising containment ring structures 1835 and 1840 configured to contain the immobilized reagent-substrate-polymer layer. For example, the immobilized reagent-substrate-polymer layer (as discussed above with respect to FIGS. 12, 13A, 13B, and 13C) may be deposited onto at least a portion of the sensors 1805 and/or 1810 within the containment ring structures 1835 and/or 1840. The wirings 1815 and 1825 terminate at the first amperometric pin 1820 and the second amperometric pin 1830 respectively, which are used to make contact with a connector in an analyzer or cartridge reader (e.g., an i-STAT® cartridge reader as described in U.S. Pat. No. 4,954,087).

In some embodiments, the silicon chip 1800 further includes an integrated reference electrode 1845. In accordance with aspects of the present invention, in which the sensors 1805 and 1810 are amperometric sensors, the reference electrode 1845 is configured as a counter electrode to complete the circuitry. The reference electrode 1845 may comprise silver metal (Ag) and its silver salt (AgCl) deposited on a solid substrate (i.e., a Ag/AgCl reference electrode). The reference electrode may be connected via wiring 1850 to an AC ground and reference pin 1855 (e.g., temporary electrical connector). The wiring 1850 may be formed with a gold surface that is coated with a photo defined polyimide or photoresist layer such that the wiring 1850 is insulated from exposure to the biological sample disposed within the channel. In preferred embodiments, the reference electrode 1845 is designed in a checkerboard pattern as illustrated in FIG. 18 to improve wettability of a surface of the reference electrode 1845. Specifically, it has been found unexpectedly that the wettability of the reference electrode 1845 may be improved using the checkerboard pattern because AgCl is relatively hydrophobic and can promote the formation of an air bubble over the surface of the reference electrode 1845 when a solid patch of AgCl is used, which results in a poor circuit.

Figure 19:
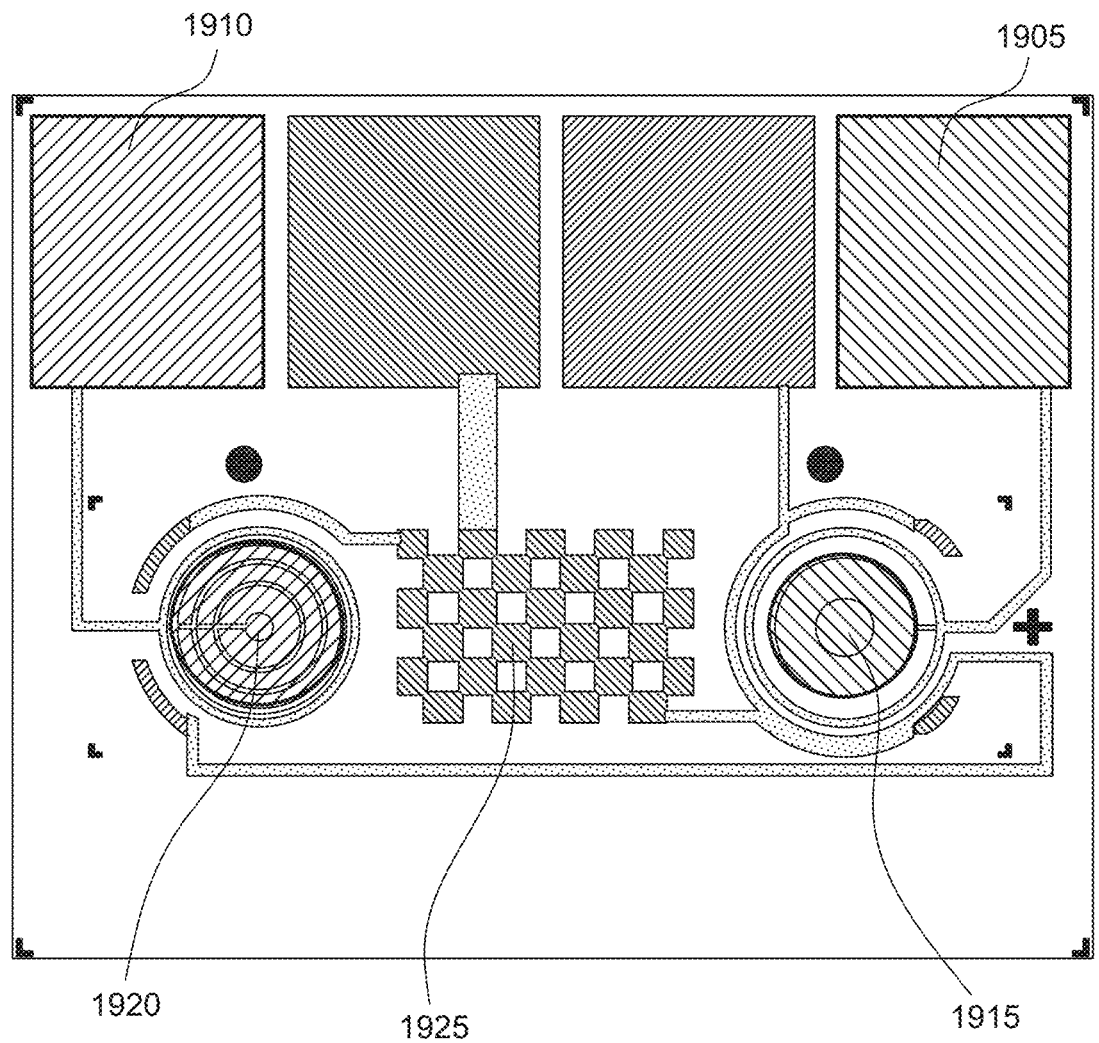

As discussed in detail above with respect to the silicon chip 1800 and as shown in FIG. 19, in the preferred embodiments of the present invention the analyzer applies a potential via the first amperometric pin 1905 and the second amperometric pin 1910 between each of the amperometric sensors 1915 and 1920 and the reference electrode 1925, and measures current changes generated by cleaved substrate as an electrochemical signal. The electrochemical signal being proportional to the concentration of the product in the biological sample. The amperometric sensors 1915 and 1920 have an applied potential of approximately +0.4 V versus the reference electrode 1925 and, in another preferred embodiment, the amperometric sensors 1915 and 1920 have an applied potential of approximately +0.1 V versus the reference electrode 1925. The signal generated by the enzyme reaction product at approximately +0.1V is distinguishable from the signal generated by the unreacted substrate at approximately +0.4 V.

With reference back to FIG. 18, in some embodiments, the silicon chip 1800 may further include conductometric sensors 1860 and 1865 (which can also function as hematocrit sensors). The conductometric sensors 1860 and 1865 may be split to form two sensor pairs with one at each end of the chip 1800. The conductometric sensors 1860 and 1865 are configured to determine biological sample arrival and/or departure at the amperometric sensors 1805 and 1810, respectively. More specifically, the conductometric sensors 1860 and 1865 lie in an arc that is perpendicular to a length of the channel or sensor channel, and an electrical resistance between pairs of electrodes for each sensor may be used to monitor a relative position of a fluid front of the biological sample. At the extremes, an open circuit reading indicates that the biological sample has been pushed off the amperometric sensors 1805 and 1810 and a closed circuit reading indicates the amperometric sensors 1805 and 1810 are covered with the biological sample.

Figure 20:
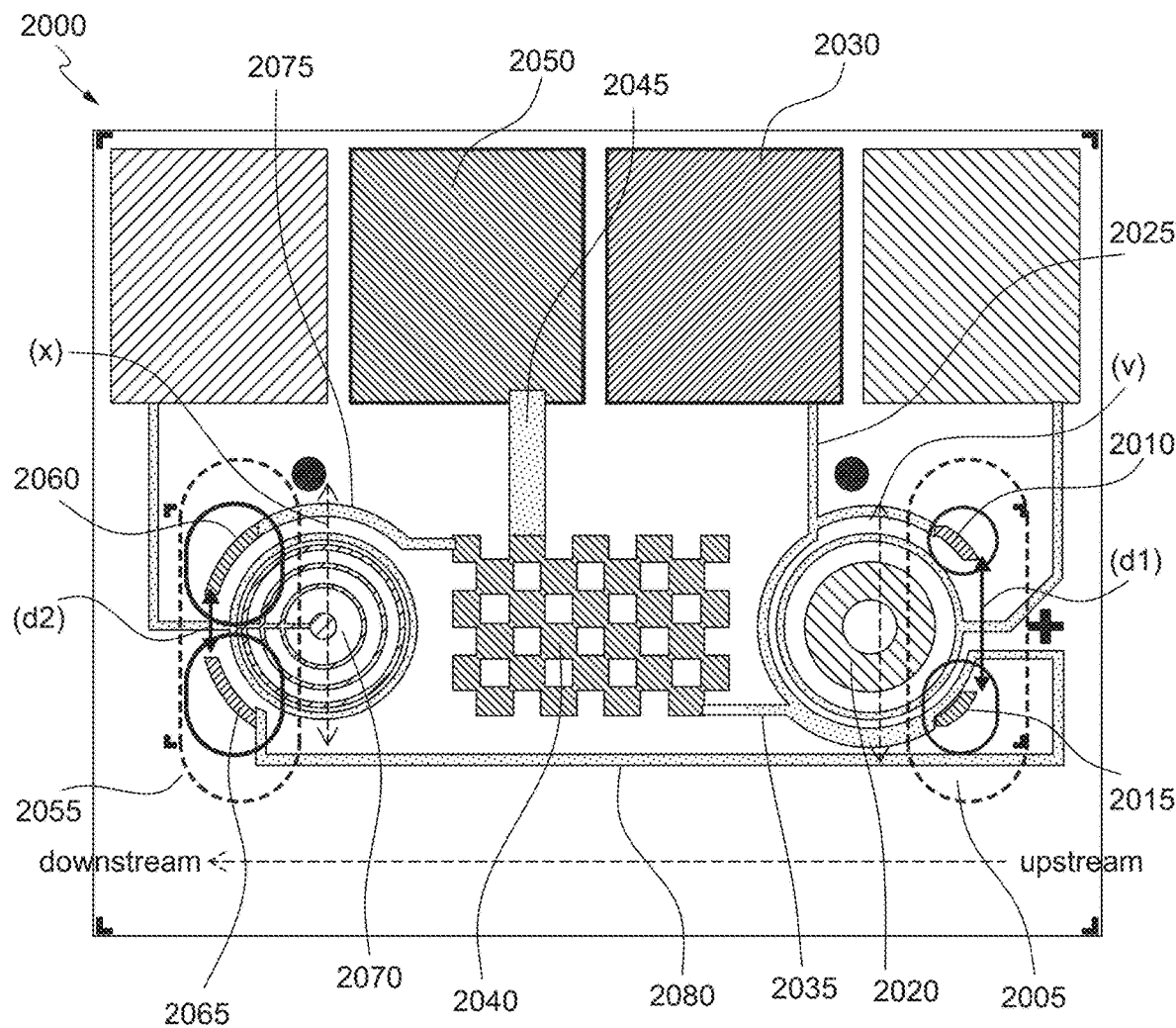

As shown in FIG. 20, the conductometric sensor 2005 may comprise at least two electrodes 2010 and 2015 (i.e., first electrode pair) positioned at a predetermined distance (d1) from one another. In some embodiments, the conductometric sensor 2005 may be positioned on the silicon chip 2000 relative to a midpoint (v) of the amperometric sensor 2020 (e.g., upstream, downstream, or in-line with the midpoint (v)). The electrode 2010 may be connected via wiring 2025 to an AC source pin 2030 (e.g., temporary electrical connector). The electrode 2015 may be connected via wiring 2035, the reference electrode 2040, and the wiring 2045 to the AC ground and reference pin 2050. The wirings 2025 and 2035 may be formed with a gold surface that is coated with a photo defined polyimide or photoresist layer such that the wirings 2025 and 2035 are insulated from exposure to the biological sample disposed within the channel.

The conductometric sensor 2055 may comprise at least two electrodes 2060 and 2065 (i.e., second electrode pair) positioned at a predetermined distance (d2) from one another. In some embodiments, the conductometric sensor 2055 may be positioned on the silicon chip 2000 relative to a midpoint (x) of the amperometric sensor 2070 (e.g., upstream, downstream, or in-line with the midpoint (x)). The electrode 2060 may be connected via wiring 2075, the reference electrode 2040, and the wiring 2045 to the AC ground and reference pin 2050. The electrode 2065 may be connected via wiring 2080 and the wiring 2025 to the AC source pin 2030. The wirings 2075 and 2080 may be formed with a gold surface that is coated with a photo defined polyimide or photoresist layer such that the wirings 2075 and 2080 are insulated from exposure to the biological sample disposed within the channel.

Figure 21:
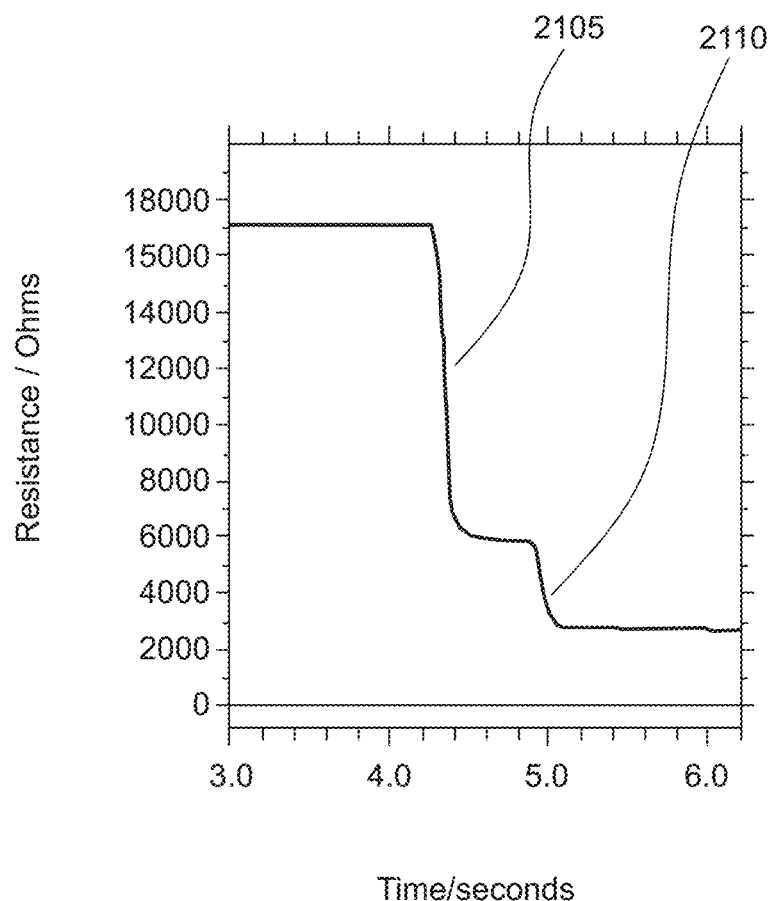
FIGS. 21, 22A, and 22B illustrate the principle of operation for conductometric sensors in accordance with various embodiments.

In preferred embodiments, the conductometric sensors 2005 and 2055 are configured to detect arrival of the biological sample within the channel at the amperometric sensors 2020 and 2070, respectively. As shown in FIG. 21 (with reference to FIG. 20), the arrival of the biological sample at the amperometric sensors 2020 and 2070 may be detected based on determination of a first resistance drop 2105 when the biological sample reaches conductivity sensor 2005 and a second resistance drop 2110 when the biological sample reaches conductivity sensor 2055. In additional or alternative embodiments, determination of a rise or spike (not shown) in the resistance at either or both of the conductometric sensors 2005 and 2055 may be used to detect the presence of an air bubble within the channel that is positioned over either or both of the amperometric sensors 2020 and 2070.

Figure 22A:
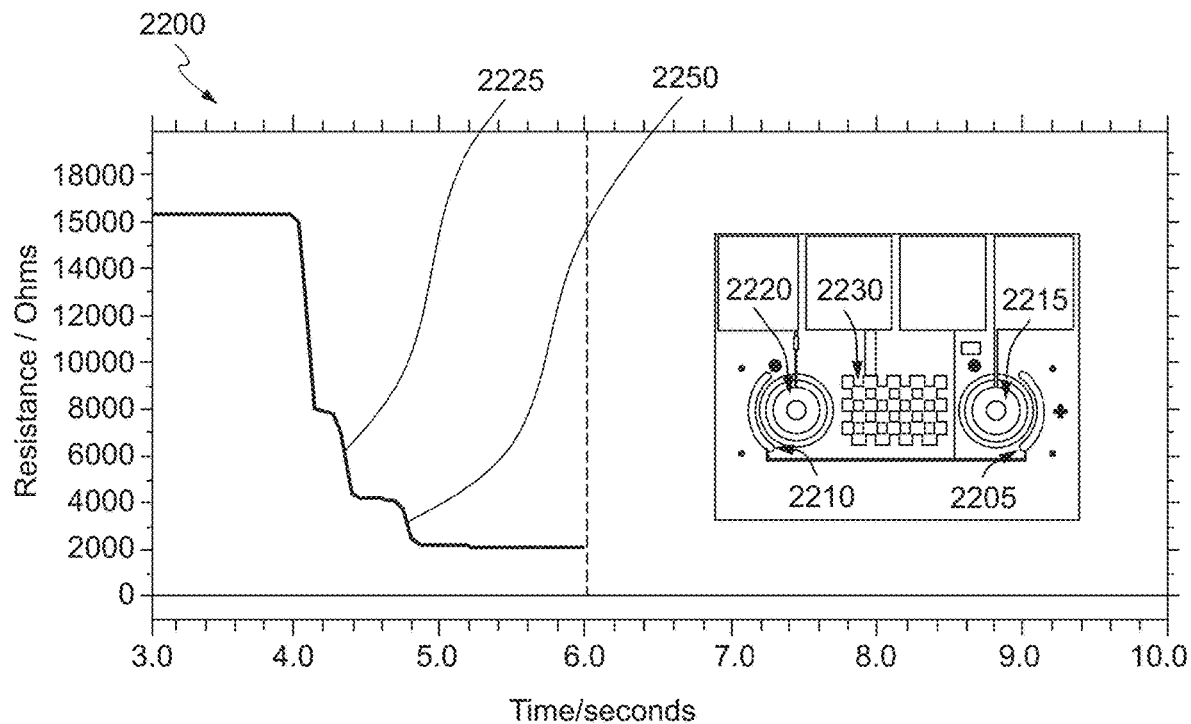

A resistance profile for the conductometric sensors 2005 and 2055 should preferably provide two well defined resistance drops of roughly equal amplitude. In some chip designs, as shown in FIG. 22A, conductometric sensors 2205 and 2210 may be configured as separate bars on opposite ends of the chip near respective amperometric sensors 2215 and 2220. However, the resistance profile 2200 for such a design is found to often include an additional step 2225, which is attributable to the sample temporarily stopping on the reference electrode 2230 due to the hydrophobic nature of the reference electrode 2230. As should be understood, this could make it difficult to decipher the second resistance drop as either the wetting of the reference electrode 2230 or the sample arriving at the second conductometric sensor 2210. Additionally, the time between the two steps is quite short, making the timing difficult, and the resistance drop of the second arrival is much smaller compared to the first drop, making the detection difficult.

Figure 22B:
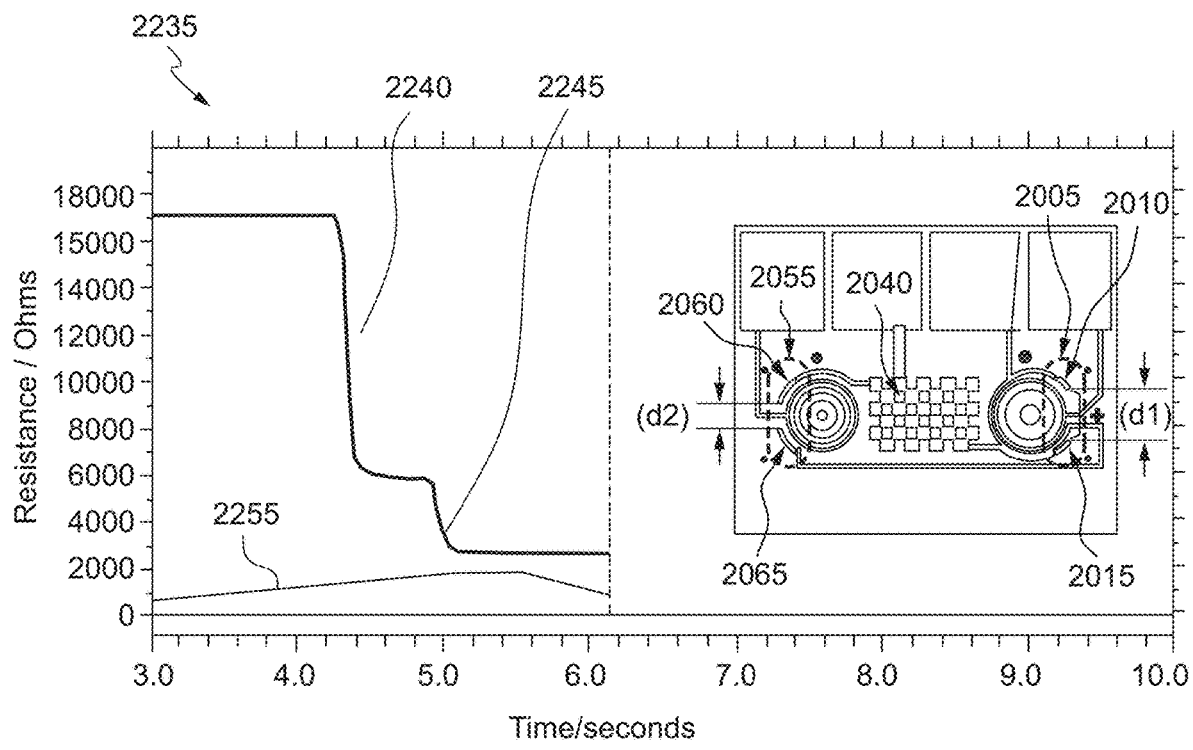

Accordingly, as shown in FIG. 22B (with reference to FIG. 20), the chip design implemented in preferred embodiments of the present invention utilizes the conductometric sensors 2005 and 2055, which are each split to comprise at least two electrodes 2010, 2015 and 2060, 2065 spaced apart at predetermined distances (d1) and (d2), respectively. As illustrated in the resistance profile 2235, the dominant resistance drops 2240 and 2245 occur at the two pairs of conductometric sensors 2005 and 2055. Thus, reducing the impact of the additional resistance drop 2225 (shown in FIG. 22A) observed from the wetting of the reference electrode 2040. Further, the conductometric sensors 2005 and 2055 are placed at a front and rear of the chip to increase a time between the resistance drops 2240 and 2245 to better differentiate the resistance drops 2240 and 2245. Moreover, in some embodiments, the spacing or predetermined distance (d1) provided between the electrodes 2010 and 2015 is a value "n" greater than that of the spacing or predetermined distance (d2) provided between the electrodes 2060 and 2065 such that an amplitude of the second resistance drop 2245 is increased over a resistance drop 2250 (shown in FIG. 22A) of the alternative chip design. For example, (d1) may be constructed twice as large as that of (d2) to achieve about a 1000 ohm increase in amplitude of the second resistance drop. The increase in (d1) over that of (d2) effectively increases the ratio of resistance drops for the chip design shown in FIG. 22B over that of the ratio of resistance drops for the chip design shown in FIG. 22A. Advantageously, this increase in resistance drops allows for better detection of the arrival of the biological sample at the conductometric sensors 2005 and 2055 during an on/forward motor or pump position 2255.

In some embodiments, processes of the present invention may include continually moving the biological sample forward and back over the chip at a controlled velocity. Controlling the time for which the conductometric sensors 2005 and 2055 remain as open and closed circuits controls the position at which the biological sample changes direction. For example, a pneumatic pump or pump actuator within the analyzer may be configured to oscillate the biological sample in the channel with the trailing edge of the biological sample positioned in the region of the conductometric sensor 2005 in order to dissolve the substrate in that portion of the sample near the trailing edge. The oscillation may be at a frequency in the range of 0.2 to 10 Hertz for a period in the range of 1 to 100 seconds. In a preferred method, the oscillation may be at a frequency in the range of about 1.5 Hertz for a period of about 20 seconds. In another preferred method the oscillation may be at a frequency of about 0.3 Hertz and the amperometric sensors 2020 and 2070 (as shown in FIG. 20) may be configured to generate a signal at each oscillation. If erythrocytes or other elements such as other cell types, polymers, proteins, beads, etc. are present in the biological sample, the oscillation may be at a frequency adequate to prevent the settling of the erythrocytes or other elements on the amperometric sensors 2020 and 2070.

In some embodiments, the amperometric sensors 2020 and 2070 determine the concentration of product each time the biological sample is oscillated past the amperometric sensors 2020 and 2070. For example, a first amperometric sensor signal may be stored by the analyzer for each of the amperometric sensors 2020 and 2070 and subsequent signals from the amperometric sensors 2020 and 2070 may be stored and compared to the first and other stored signals in order to determine a maximum rate of change in the amperometric sensor signals. These data points may then be analyzed to determine a fixed fraction of a maximum rate of change of the amperometric sensor signals. These data points may thus be used to determine a coagulation parameter of interest for each of the amperometric sensors 2020 and 2070.

In alternative embodiments, the sensors or transducers may be formed as an optical detector, (e.g., CCD camera chip) and optical wave guide. The optical detector may either be a detector of fluorescence, chemiluminescence, or bioluminescence emission from the detectable moiety or a detector of absorbance by the detectable moiety. In such embodiments, the detectable moiety may be an optical dye, a fluorescence emitter, chemiluminescence emitter or a bioluminescence emitter.

In other embodiments, the sensor or transducers may be formed as a test strip, (e.g., a glucose test strip, as described in U.S. patent application Ser. No. 13/724,348), which is incorporated herein in its entirety. For example, a test strip may be included within the cartridges described herein. In some embodiments, the sample may be manually placed on the test strip and, as such, the microfluidic systems described herein would not need to be included with such embodiments. As is well known in the art, glucose test strip devices can include passive capillary fluidic elements to deliver the sample to a sensor or sensor array. As such, the elements, features, and functionality of a glucose test strip could be adapted to the present invention without departing from the spirit and scope of the present invention.

Systems and Processes for Sample Analysis

Figure 23:
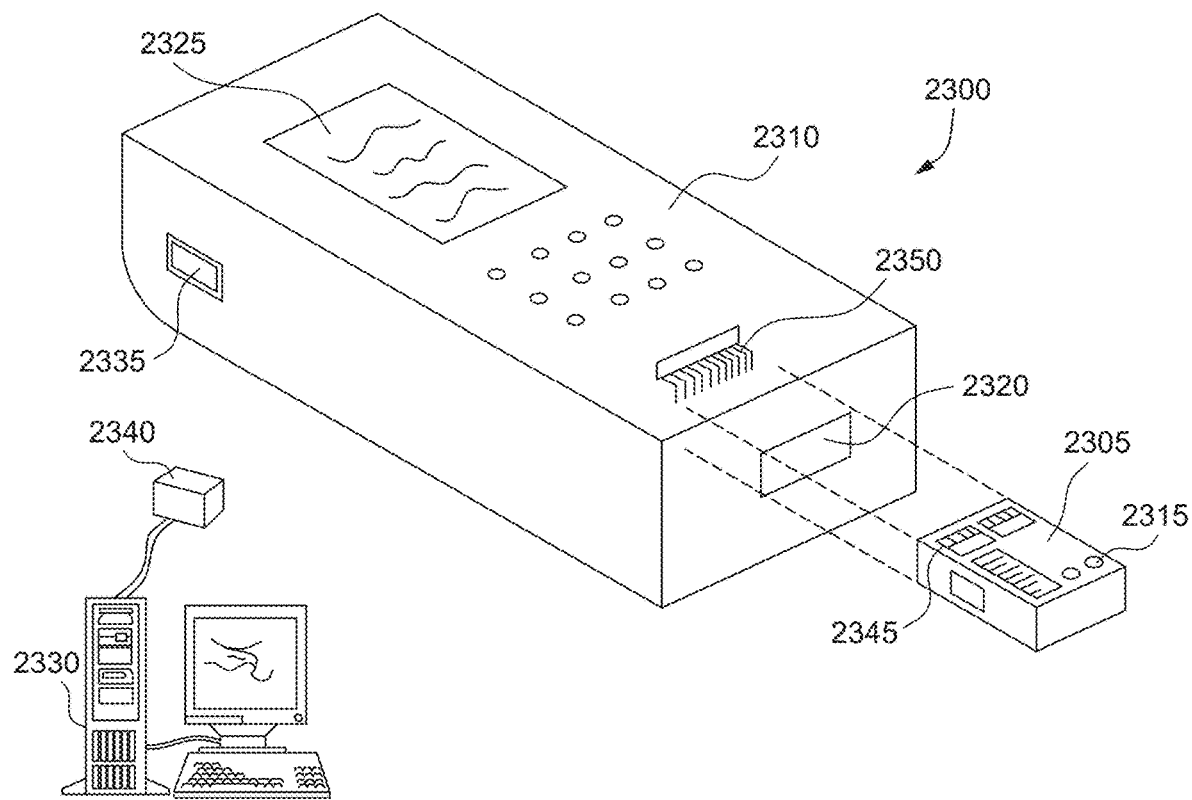
FIG. 23 shows an isometric view of a disposable sensing device and reader device in accordance with various embodiments.

As shown in FIG. 23, a system 2300 may comprise a self-contained disposable sensing device or cartridge 2305 and a reader device or instrument 2310 (e.g., an analyzer). In some embodiments, the cartridge 2305 is a single-use device configured to be disposable after the single-use. A fluid sample (e.g., whole blood) to be measured is drawn into a sample entry orifice or port 2315 in the cartridge 2305, and the cartridge 2305 may be inserted into the reader 2310 through a slotted opening 2320. The reader 2310 may comprise a processor configured to perform measurements of analyte concentrations, measurements of resistances, identify analytes or sets of analytes that a chip is configured to measure, and/or determinations of diagnostic clotting time within the fluid sample, as discussed herein in further detail. Measurements and determinations performed by the reader 2310 may be output to a display 2325 or other output device, such as a printer or data management system 2330 via a port 2335 on the reader 2310 to a computer port 2340. Transmission can be via Wifi, Bluetooth link, infrared and the like. In embodiments where the sensors 2345 in the cartridge 2305, (e.g., micro-environment sensors), are based on electrochemical principles of operation, (e.g., a first sensor and optionally a second sensor) may be configured to make electrical contact with the reader 2310 via an electrical connector 2350. For example, the connector may be of the design disclosed in jointly owned U.S. Pat. No. 4,954,087, incorporated herein by reference in its entirety. In some embodiments, the PT and aPTT sensors may be configured to connect with an electrical connector of a test meter within the reader 2310 via the electrical connector 2350 (see, e.g., U.S. Pat. Nos. 5,096,669 and 4,954,087, incorporated herein by reference in their entireties). The reader 2310 may also include a method for automatic fluid flow compensation in the cartridge 2305, as disclosed in jointly owned U.S. Pat. No. 5,821,399, which also is incorporated herein by reference in its entirety.

Figure 24A:
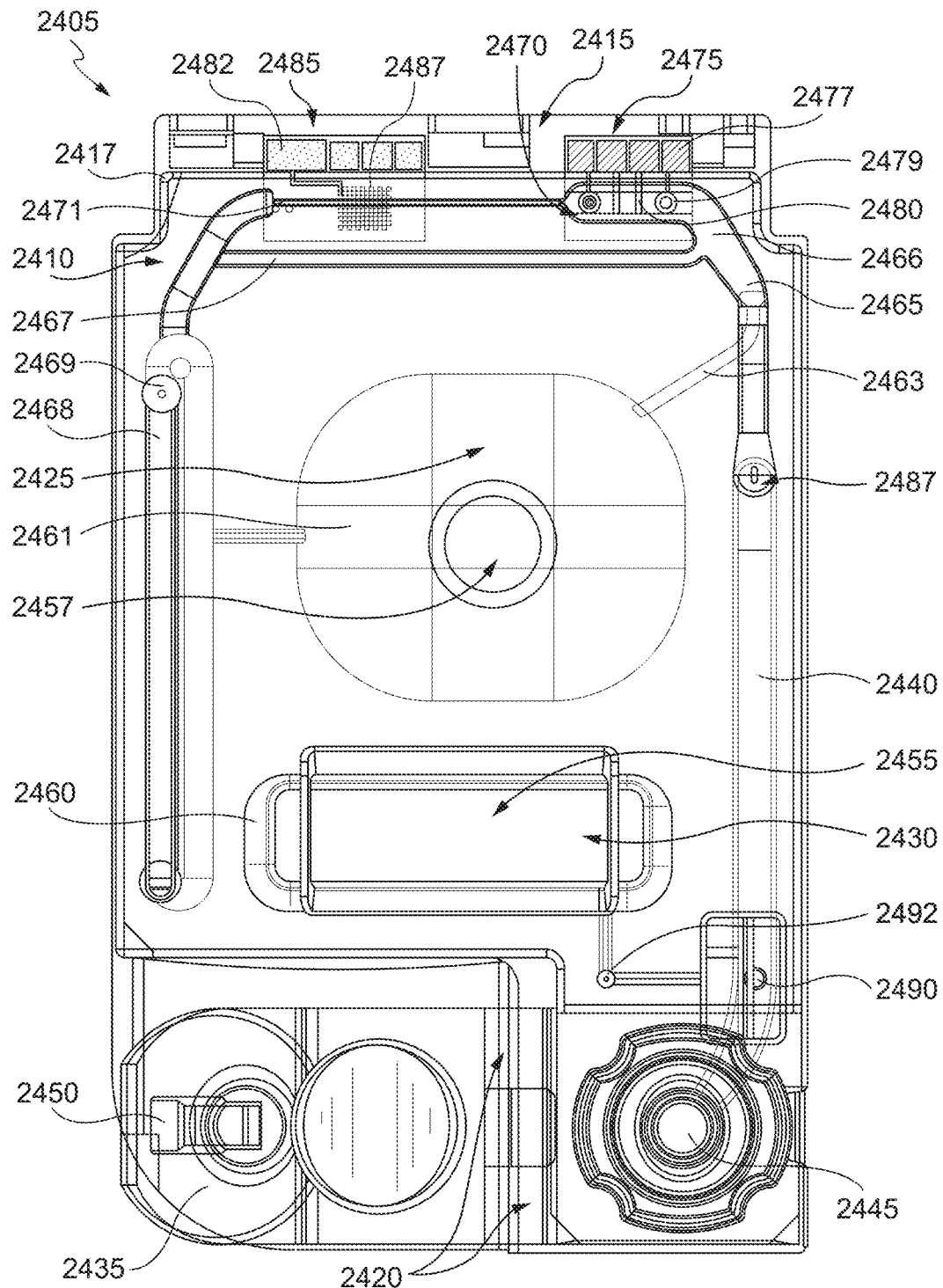
FIG. 24A shows a top view of a disposable sensing device in accordance with various embodiments.
Figure 24B:
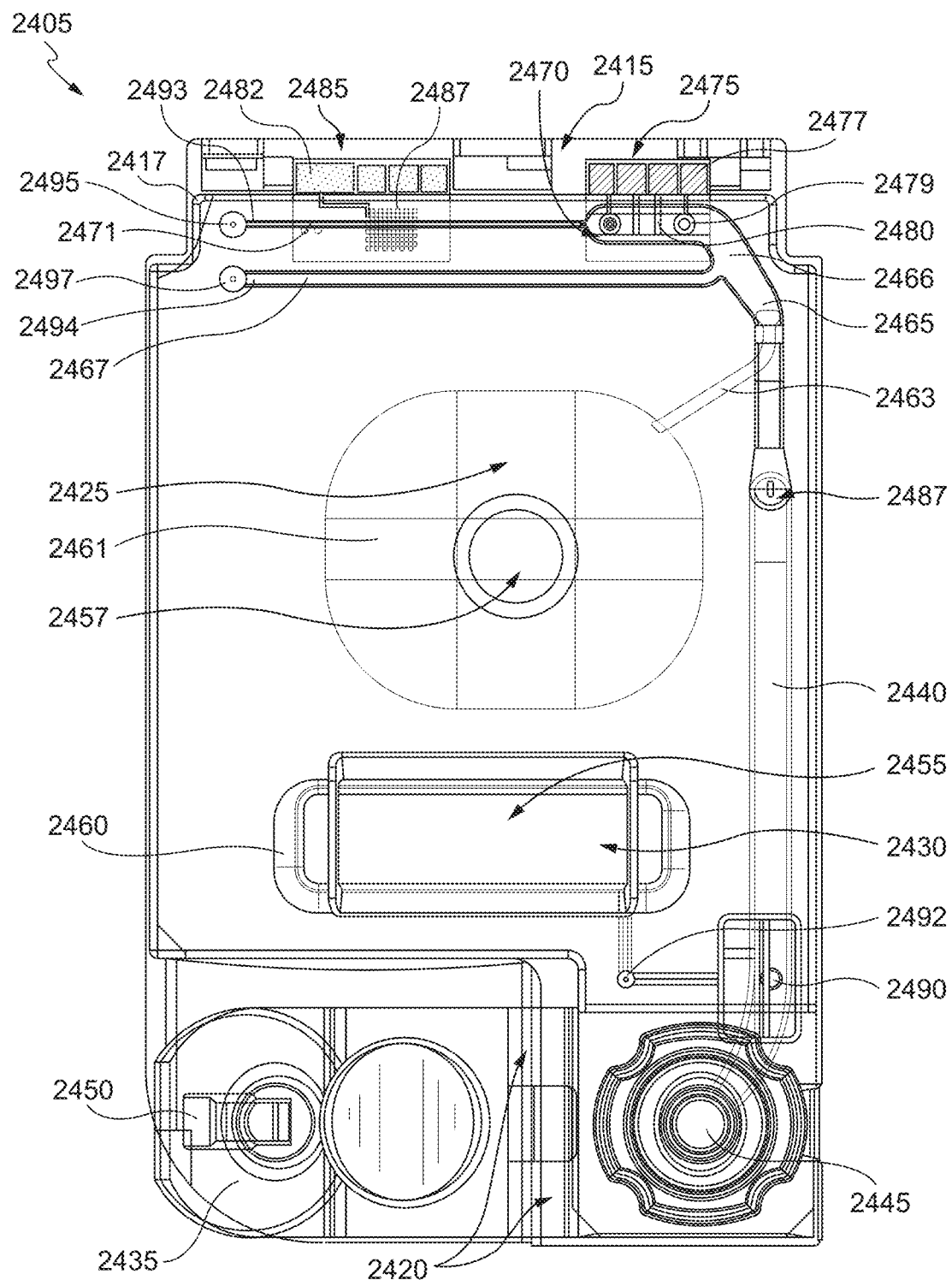
FIG. 24B shows a top view of an alternative disposable sensing device in accordance with various embodiments.

As shown in FIGS. 24A and 24B, a self-contained disposable sensing device or cartridge 2405 may comprise a plurality of microfluidic channels and chambers configured to move one or more fluids through the cartridge 2405 for purposes of performing one or more analytical tests. In various embodiments, as shown in FIG. 24A, a self-contained disposable sensing device or cartridge 2405 has a housing comprising a cover 2410 (e.g., a first plastic member), a base 2415 (e.g., a second plastic member), and a thin-film adhesive gasket 2417 (e.g., a double-sided adhesive tape gasket member) that is disposed between the base 2415 and the cover 2410. One or more of the cover 2410, the base 2415, and the gasket 2417 define the various channels and junctions of the cartridge 2405. The cartridge 2405 may be configured for insertion into a reader, and therefore the cartridge 2405 may comprise a plurality of mechanical and electrical connections (not shown) for this purpose. Advantageously, a feature of the cartridge 2405 is that once a fluid or biological sample is loaded within the cartridge 2405, analysis of the fluid or biological sample may be completed and the cartridge 2405 may be discarded without an operator or others contacting the fluid or biological sample.

In some embodiments, the cover 2410 may be made of a rigid material, preferably plastic, and capable of repetitive deformation at flexible hinge regions 2420, 2425, and 2430 without cracking. The cover 2410 may comprise a lid 2435, attached to a main body of the cover 2410 by the flexible hinge 2420. In operation, after introduction of the fluid or biological sample into a sample holding chamber 2440 through a sample entry port 2445, the lid 2435 may be secured over an entrance to the sample entry port 2445, preventing sample leakage. The lid 2435 may be held in place by a hook 2450. The cover 2410 may further comprise a first deformable member 2455 and an optional deformable member 2457 that are moveable relative to the body of the cover 2410, and which may be attached to the cover 2410 by the flexible hinge regions 2430 and 2425, respectively.

The deformable member 2455 may be operated upon by a first pumping means (e.g., an actuating arm) such that a force is exerted upon an air bladder comprised of cavity 2460 and optionally the gasket 2417. In some embodiments, deformation of the deformable member 2455 displaces fluid within channels of the cartridge 2405. The deformable member 2457 may be operated upon by a second pumping means (e.g., an actuating arm) such that a force is exerted upon an air bladder comprised of cavity 2461 and optionally the gasket 2417. In some embodiments, deformation of the deformable member 2457 displaces fluid within channels of the cartridge 2405. In other embodiments, deformation of the deformable member 2457 transmits pressure onto a fluid-containing foil pack filled with a fluid, (e.g., approximately 130 μL of analysis/wash solution, a control fluid, or calibrant fluid), located in cavity 2461, rupturing the foil pack, and expelling fluid into channel 2463 for subsequent use in other channels during sample analysis. As should be understood, while coagulation assay formats do not generally require the use of these fluids, the fluids may generally be required in a single device that combines coagulation tests with other tests, e.g., a wash fluid in immunoassays for analytes such as BNP and troponin, and a calibrant fluid in chemistry tests such as potassium, creatinine and glucose. In other embodiments, the second pumping means may not operate upon the deformable member 2457, and instead, the cavity 2461 may be configured as a waste chamber. In other embodiments, the second pumping means may not be present, and the cavity 2461 is absent from the cartridge 2405.

Additional action in the cartridge 2405 generated by mechanisms within the reader (discussed with respect to FIG. 23) applied to the cartridge 2405 may be used to inject one or more air segments into the fluid or biological sample at controlled positions within the sample holding chamber 2440 and subsequent channels 2465 (lead channel), 2466 (sensor channel), and 2467 (bypass channel). The air segments may be used to wash a sensor surface of the sensor array and the surrounding channel 2466 with a minimum amount of fluid (e.g., a limited wash cycle in which the volume of wash may be less than fifty times a volume of the fluid or biological sample and/or fewer than three independent cycles of clean wash buffer (e.g., three independent washing steps with fresh wash buffer)), as should be understood by those of ordinary skill in the art of immunoassay procedures. For example, the cover 2410 may further comprise a hole covered by a thin pliable film. In operation, pressure exerted upon the film may expel one or more air segments into the channel 2466 through a small hole in the gasket.

In some embodiments, a lower surface of the cover 2410 further comprises sample holding chamber 2440, the channels 2465, 2466, and 2467 and another channel 2468 (e.g., a waste channel). The sample holding chamber 2440 and the channels 2465, 2466, and 2467 may include one or more constrictions or capillary stops 2470 and 2471 that control fluid flow by providing resistance to the flow of the fluid or biological sample. Optional coatings (not shown), (e.g., dry reagent coatings), may provide hydrophobic surfaces on the sample holding chamber 2440 and the channels 2465, 2466, and 2467, which together with gasket holes may control fluid flow between the sample holding chamber 2440 and the channels 2465, 2466, and 2467. The sample holding chamber 2440 may be configured to connect the sample entry port 2445 to the channels 2465, 2466, and 2467 in the assembled cartridge 2405. In some embodiments, the channel 2468 includes a vent hole 2469 that allows gases (e.g., gas pressure) within the channels 2465, 2466, and 2467 to be released outside the cartridge 2405 to the atmosphere, which together with dimensional design of the channels, controls fluid flow between the sample holding chamber 2440 and the channels 2465, 2466, and 2467.

In accordance with various embodiments in which there are multiple chips (e.g., a ground chip and a sensor chip), the cutaway 2475 may house one or more sensor chips 2477 comprising at least one sensor 2479 (e.g., a PT, aPTT, or ACT micro-environment sensor), or a responsive surface, together with an optional conductometric sensor or sensors 2480. A cutaway 2482 may house a ground chip 2485 comprising a ground electrode 2486 if needed as a return current path for an electrochemical sensor, and may also house an optional conductometric sensor. In accordance with various embodiments in which there is only a single chip, (e.g., a combined ground and sensor chip) the cutaway 2482 and the ground chip 2485 may not be included with the cartridge 2405, and instead the ground electrode 2486 is included on the one or more sensor chips 2477 in the cutaway 2475.

In some embodiments, a metering means may be provided that comprises the sample holding chamber 2440 bounded by the constriction or capillary stop 2487 and having along the sample holding chamber 2440 length an air entry point 2490 from the bladder comprising cavity 2460. Air pressure exerted at the entry point 2490 drives a metered volume of the sample past the constriction or capillary stop 2487. Therefore, a metered volume of sample may be predetermined by a volume of the sample holding chamber 2440 between the air entry point 2490 and the constriction or capillary stop 2487. An amount of the sample corresponding to this volume may be displaced into the channels 2465, 2466, and 2467 when the deformable member 2455 is displaced. This arrangement may therefore provide a metering means for delivering a metered amount of an unmetered sample into the various downstream channels of the cartridge 2405. The metering may be advantageous in some embodiments if quantization of an analyte is required. Thus, an operator may be relieved of accurately measuring the volume of the sample prior to measurement saving time, effort, and increasing the accuracy and reproducibility.

In various embodiments, a process is provided for using a cartridge (e.g., cartridge 2405) to determine a quantitative measurement of a target analyte or diagnostic clotting times in a whole blood sample. The process may include introducing an unmetered fluid sample into the sample holding chamber 2440 of the cartridge 2405 through the sample entry port 2445 (as shown in FIG. 24A). Capillary stop 2487 prevents passage of the fluid sample into the channels 2465, 2466, and 2467 at this stage, and the sample holding chamber 2440 is filled with the sample. Lid 2435 is closed to prevent leakage of the fluid sample from the cartridge 2405. The cartridge 2405 may then be inserted into the reading device or apparatus, as shown in FIG. 23 and further disclosed in U.S. Pat. No. 5,821,399, which is incorporated herein by reference in its entirety. In some embodiments, insertion of the cartridge into the reading apparatus activates the second pumping means, which creates a force upon the deformation member 2457 and punctures the fluid-containing package located in the cavity 2461 when the package is pressed against a spike (not shown). Fluid may thereby be expelled into one or more channels (e.g., channel 2463) arriving in sequence at the sensor region. Thereafter, operation of the first pumping means (e.g., an actuation arm of a pneumatic pump) deforms the deformable member 2455 and applies a force or pressure to the cavity 2460, forcing air through a channel 2492 into the sample holding chamber 2440 at the air entry point 2490. Capillary stop 2487 delimits a metered portion of the original fluid sample. The metered portion of the sample is then expelled through the capillary stop 2487 by air pressure produced by first pumping means and the deformable member 2455. The sample passes into the channels 2465, 2466, and 2467 and into contact with the one or more reagents, the one or more substrates (e.g., an immobilized reagent-sub strate-polymer layer), and/or the one or more sensors 2479 comprising one or more transducers and optionally the ground electrode 2486 located on ground chip 2485.

In alternative embodiments, as shown in FIG. 24B, the self-contained disposable sensing device or cartridge 2405 has a housing comprising the cover 2410 (e.g., a first plastic member), the base 2415 (e.g., a second plastic member), and the thin-film adhesive gasket 2417 (e.g., a double-sided adhesive tape gasket member) that is disposed between the base 2415 and the cover 2410. One or more of the cover 2410, the base 2415, and the gasket 2417 define the various channels and junctions of the cartridge 2405 as described in detailed with respect to FIG. 24A. However, in alternative embodiments, the another channel 2468 (e.g., a waste channel) and vent hole 2469 are removed from the cartridge 2405. Instead, the channel 2466 terminates at a first terminal end 2493 and the channel 2467 terminates at a second terminal end 2494. In some embodiments, the channel 2466 includes a vent hole 2495 (e.g., a vent hole 2495 positioned at the terminal end 2493) that allows gases (e.g., gas pressure) within the channels 2465 and 2466 to be released outside the cartridge 2405 to the atmosphere, which together with dimensional design of the channels, controls fluid flow between the sample holding chamber 2440 and the channels 2465, 2466, and 2467. In some embodiments, the channel 2467 includes a vent hole 2497 (e.g., a vent hole 2497 positioned at the terminal end 2494) that allows gases (e.g., gas pressure) within the channels 2465 and 2467 to be released outside the cartridge 2405 to the atmosphere, which together with dimensional design of the channels, controls fluid flow between the sample holding chamber 2440 and the channels 2465, 2466, and 2467.

Fluidic Function and Bypass Channel Configuration

Figure 25A:
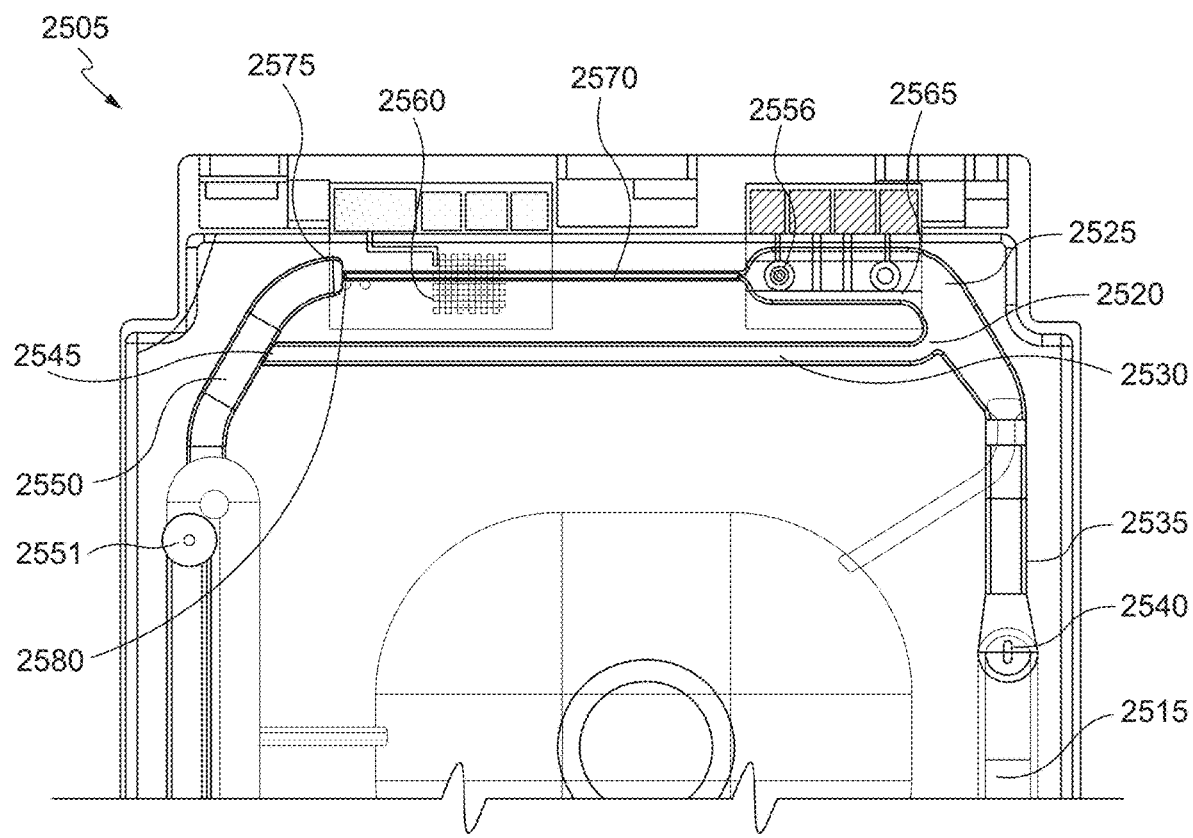
FIG. 25A shows a top view of a portion of disposable sensing devices in accordance with various embodiments.
Figure 25B:
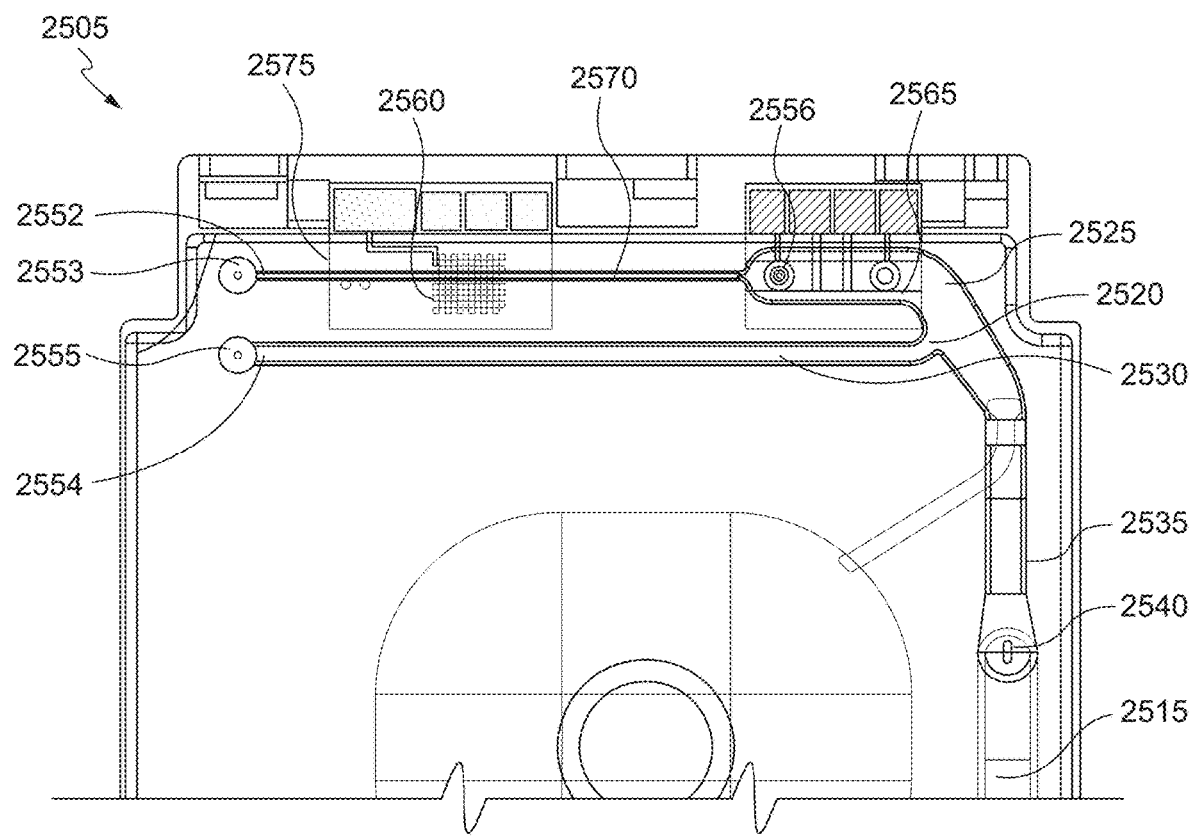
FIG. 25B shows a top view of an alternative portion of disposable sensing devices in accordance with various embodiments.

In various embodiments, disposable cartridge configurations shown in FIGS. 25A and 25B are provided for that mitigate the drift of fluid samples over a sensor by incorporating a bypass channel into the microfluidics. In some embodiments, the fluid sample is a biological sample such as blood, diluted blood, plasma, diluted plasma, serum, diluted serum, urine, diluted urine, saliva, diluted saliva, cerebrospinal fluid, diluted cerebrospinal fluid, lysed cells, or the like; or the fluid sample is an artificial sample such as an aqueous control fluid, diluted control fluid, calibrant fluid, diluted calibrant fluid, or the like. As shown in FIG. 25A, a self-contained disposable sensing device or cartridge 2505 (e.g., the cartridge 2405 described with respect to FIG. 24A or 24B) comprises a fluid sample entry port (e.g., the entry port 2445 described with respect to FIG. 24A or 24B) and holding chamber 2515 connected to a bifurcation junction 2520 of a first channel 2525 (e.g., a sensor channel) and a second channel 2530 (e.g., a bypass channel). In some embodiments, a lead channel 2535 (e.g., a lead channel) is provided between the holding chamber 2515 and the bifurcation junction 2520. For example, the lead channel 2535 may define the channel area between a constriction or capillary stop 2540 and the bifurcation junction 2520. In some embodiments, the first channel 2525 and the second channel 2530 are connected at a recombination junction 2545 to a third channel 2550. The third channel 2550 may include a vent 2551. For example, the first channel 2525 may define a first channel area between the bifurcation junction 2520 and the recombination junction 2545; and the second channel 2530 may define a second channel area between the bifurcation junction 2520 and the recombination junction 2545. In other embodiments, as shown in FIG. 25B, the first channel 2525 terminates at a first terminal end 2552 and comprises a vent 2553, for example a vent 2553 at the first terminal end 2552 and the second channel 2530 terminates at a second terminal end 2554 and comprises a vent 2555, for example, a vent 2555 at the second terminal end 2554. The first channel may include one or more sensors 2556 (e.g., a micro-environment sensor) and optionally a ground sensor 2560.

A width of the holding chamber 2515 is in the range from 0.5 mm to 5.0 mm or from 1.0 mm to 2.0 mm, for example about 2.0 mm. A height of the holding chamber 2515 is in the range from 0.05 mm to 2.0 mm or from 0.1 mm to 0.5 mm, for example about 0.25 mm. A length of the holding chamber 2515 is in the range from 5 mm to 20 mm or from 7 mm to 15 mm, for example about 12 mm. A volume of the holding chamber 2515 is in the range from 5 μL to 200 or from 10 μL to 50 for example about 10 μL. The cross-sectional area of the holding chamber 2515 is in the range from 0.1 $mm^2$ to 50 $mm^2$ or from 0.1 $mm^2$ to 20 $mm^2$, for example about 20 $mm^2$. A width of the lead channel 2535 is in the range from 0.5 mm to 5.0 mm or from 2.0 mm to 4.5 mm, for example about 2.0 mm. A height of the lead channel 2535 is in the range from 0.05 mm to 2.0 mm or from 0.1 mm to 1.0 mm, for example about 0.25 mm. A length of the lead channel 2535 is in the range from 0.5 mm to 10 mm or from 2 mm to 7 mm, for example about 2.5 mm. A volume of the lead channel 2535 is in the range from 0.5 μL to 50 μL or from 2.5 μL to 25 for example about 3.5 μL. The cross-sectional area of the lead channel 2535 is in the range from 0.1 $mm^2$ to 20 $mm^2$ or from 0.5 $mm^2$ to 10 $mm^2$, for example about 10 $mm^2$. All ranges disclosed herein are to be understood to encompass any and all subranges subsumed therein. For example, a stated range of "1 to 10" should be considered to include any and all subranges between (and inclusive of) the minimum value of 1 and the maximum value of 10; that is, all subranges beginning with a minimum value of 1 or more, (e.g., 1 to 6.1), and ending with a maximum value of 10 or less, e.g., 5.5 to 10. As used herein, the terms "substantially," "approximately" and "about" are defined as being largely but not necessarily wholly what is specified (and include wholly what is specified) as understood by one of ordinary skill in the art. In any disclosed embodiment, the term "substantially," "approximately," or "about" may be substituted with "within [a percentage] of" what is specified, where the percentage includes 0.1, 1, 5, and 10 percent.

In some embodiments, the first channel 2525 comprises an upstream region 2565 and a downstream region 2570. In certain embodiments, the upstream region 2565 of the first channel includes the one or more sensors 2556 in an arrangement, as described herein with respect to FIGS. 14-22B. A width of the upstream region 2565 of the first channel 2525 is in the range from 0.5 mm to 5.0 mm or from 1.5 mm to 3.0 mm, for example about 1.5 mm. A height of the upstream region 2565 of the first channel 2525 is in the range from 0.05 mm to 1.5 mm or from 0.1 mm to 1.0 mm, for example about 0.25 mm. A length of the upstream region 2565 of the first channel 2525 is in the range from 1 mm to 25 mm or from 4 mm to 15 mm, for example about 4.8 mm. A volume of the upstream region 2565 of the first channel 2525 is in the range from 0.5 to 50 μL or 1.5 μL to 25 for example about 2.0 μL. The cross-sectional area of the upstream region 2565 of the first channel 2525 is in the range from 0.1 $mm^2$ to 20 $mm^2$ or from 1.0 $mm^2$ to 10 $mm^2$, for example about 5.75 $mm^2$. A flow rate of the upstream region 2565 of the first channel 2525 is in the range from 0.1 mm/s to 40.0 mm/s or from 2.5 mm/s to 15.0 mm/s, for example about 5.0 mm/s. In certain embodiments, the flow rate is substantially independent of one or more properties including: (i) viscosity in the range from about 0.8 mPa·s to about 3 mPa·s, for example about 1.2 mPa·s; (ii) total cellular content in the range from 0 to 80%, for example about 45%.; or (iii) hematocrit in the range from 0 to 80%, for example about 40%. A capillarity of the upstream region 2565 of the first channel 2525 is greater than a capillarity of the downstream region 2570 of the first channel 2525. As used herein, the "capillarity" is the tendency of a liquid to flow in a channel (e.g., a channel with a greater capillarity has the capability of filling easier) as a result of the channels properties including, but not limited to, its cross-section, length and hydraulic resistance. The relative capillarity of one or more channels can be determined empirically using a video camera and timer to record one or more of; (i) the relative rates of flow in the channels, (ii) into which channel a given fluid preferentially flows at a bifurcation, and (iii) the change in rate of flow at a change or discontinuity in the dimensions of a given channel.

A width of the downstream region 2570 of the first channel 2525 is in the range from 0.05 mm to 2.0 mm or from 0.1 mm to 1.0 mm, for example about 0.25 μm. A height of the downstream region 2570 of the first channel 2525 is in the range from 0.05 mm to 2.0 mm or from 0.15 mm to 1.0 mm, for example about 0.2 mm. A length of the downstream region 2570 of the first channel 2525 is in the range from 5 mm to 30 mm or from 8 mm to 15 mm, for example about 11 mm. A volume of the downstream region 2570 of the first channel 2525 is in a range from 0.5 μL to 50 μL or from 1.0 μL to 10 μL, for example about 1.5 μL. The cross-sectional area of the downstream region 2570 of the first channel 2525 is in the range from 0.1 mm$^2$ to 10 mm$^2$ or from 0.5 mm$^2$ to 7 mm$^2$, for example about 2.5 mm$^2$. A flow rate of the downstream region 2570 of the first channel 2525 is in the range from 0.1 mm/sec to 40.0 mm/sec or from 1.5 mm/s to 10.0 mm/s, for example about 3.0 mm/s. A total length of the first channel 2525 (from the bifurcation junction 2520 to the recombination junction 2545 or the first terminal end 2552) is in the range from 5 mm to 30 mm, for example about 16 mm. A total volume of the first channel 2525 (from the bifurcation junction 2520 to the recombination junction 2545 or the first terminal end 2552) is in the range from 0.5 μL to 50 μL or from 3.0 μL to 25 μL, for example about 20 μL. An overall flow rate of the first channel 2525 is in the range from 0.1 mm/s to 40.0 mm/s or from 2.0 mm/s to 18.0 mm/s, for example about 8.0 mm/s. In certain embodiments, the flow rate is substantially independent of one or more properties including: (i) viscosity in a range from about 0.8 mPa·s to about 3 mPa·s, for example about 1.2 mPa·s; (ii) total cellular content in the range from 0 to 80%, for example about 45%.; or (iii) hematocrit in the range from 0 to 80%, for example about 40%.

A width of the second channel 2530 is in the range from 0.05 mm to 3.0 mm or from 0.2 mm to 2.0 mm, for example about 0.6 mm. A height of the second channel 2530 is in the range from 0.05 mm to 2.0 mm or from 0.15 mm to 2.0 mm, for example about 0.2 mm. A length of the second channel 2530 is in a range from 1 mm to 30 mm or from 2 mm to 20 mm, for example about 18 mm. A volume of the second channel 2530 is in a range from 0.5 μL to 50 μL or from 1.0 μL to 30 μL, for example about 15 μL. The cross-sectional area of the second channel 2530 is in a range from 0.1 mm$^2$ to 15 mm$^2$ or from 1.5 mm$^2$ to 10 mm$^2$, for example about 5.0 mm$^2$. In some embodiments, the volume of the second channel 2530 is less than the total volume of the first channel 2525. In certain embodiments, the volume of the second channel 2530 is less than the total volume of the first channel 2525 by a factor in the range from 0.5 to 10, for example a factor of about 5. In other embodiments, the volume of the second channel 2530 is greater than the total volume of the first channel 2525. In certain embodiments, the volume of the second channel 2530 is greater than the total volume of the first channel 2525 by a factor in the range from 0.5 to 10, for example a factor of about 5.

A flow rate of the second channel 2530 is in the range from 0.1 mm/s to 40.0 mm/s or from 3.0 mm/s to 20.0 mm/s, for example about 5.0 mm/s. In some embodiments, a flow rate of the second channel 2530 is greater than the overall flow rate of the first channel 2525. In certain embodiments, a flow rate of the second channel 2530 is greater than an overall flow rate of the first channel 2525 by a factor in the range from 0.1 to 15, for example a factor of about 7. In certain embodiments, the flow rate is substantially independent of one or more properties including: (i) viscosity in a range from about 0.8 mPa·s to about 3 mPa·s, for example about 1.2 mPa·s; (ii) total cellular content in the range from 0 to 80%, for example about 45%.; or (iii) hematocrit in the range from 0 to 80%, for example about 40%. In some embodiments, a capillarity of the second channel 2530 is less than a capillarity of the upstream region 2565 of the first channel 2525. In certain embodiments, a capillarity of the second channel 2530 is less than a capillarity of the upstream region 2565 of the first channel 2525 by a factor in the range from 0.1 to 20, for example a factor of about 5. In some embodiments, a capillarity of the second channel 2530 is greater than a capillarity of the downstream region 2570 of the first channel 2525. In certain embodiments, a capillarity of the second channel 2530 is greater than a capillarity of the downstream region 2570 of the first channel 2525 by a factor in the range from 0.1 to 15 for example a factor of about 8.

In some embodiments, the cross-sectional area of the upstream region 2565 of the first channel 2525 is larger than the cross-sectional area of the downstream region 2570 of the first channel 2525. In certain embodiments, a ratio of the cross-sectional area of the upstream region to the cross-sectional area of the downstream region is in a range from 4:1 to 50:1 or from 6:1 to 15:1, for example a ratio of about 6:1. In some embodiments, the cross-sectional area of the second channel 2530 is less than the cross-sectional area of the upstream region 2565 of the first channel 2525. In certain embodiments, a ratio of the cross-sectional area of the second channel to the cross-sectional area of the upstream region is in a range from 0.5:1 to 1:125 or from 0.7:1 to 1:25, for example a ratio of about 0.8:1. In other embodiments, the cross-sectional area of the second channel 2530 is less than the cross-sectional area of the upstream region 2565 of the first channel 2525 and more than the cross-sectional area of the downstream region 2570 of the first channel 2525. In certain embodiments, a ratio of the cross-sectional area of the second channel to the cross-sectional area of the upstream region is in a range from 0.5:1 to 1:125 or from 0.7:1 to 1:25, for example a ratio of about 0.8:1; and a ratio of the cross-sectional area of the second channel to the cross-sectional area of the downstream region is in a range from 1.2:1 to 100:1 or from 2.0:1 to 20:1, for example a ratio of about 10:1. In other embodiments, the cross-sectional area of the second channel 2530 is more than the cross-sectional area of the downstream region 2570 of the first channel 2525. In certain embodiments, a ratio of the cross-sectional area of the second channel to the cross-sectional area of the downstream region is in a range from 1.2:1 to 100:1 or from 2.0:1 to 20:1, for example a ratio of about 10:1.

A width of the third channel 2550 is in the range from 0.5 mm to 5.0 mm or from 1.0 mm to 3.0 mm, for example about 1.0 mm. A height of the third channel 2550 is in the range from 0.05 mm to 2.5 mm or from 0.25 mm to 1.5 mm, for example about 0.25 mm. A length of the third channel 2550 is in the range from 1 mm to 16 mm or from 3 mm to 10 mm, for example about 10 mm. A volume of the third channel 2550 is in the range from 0.5 μL to 50 μL or from 1.5 μL to 20 μL, for example about 10 μL. The cross-sectional area of the third channel 2550 is in the range from 0.1 mm$^2$ to 20 mm$^2$ or from 2.0 mm$^2$ to 10 mm$^2$, for example about 8.0 mm$^2$.

In various embodiments, the self-contained disposable sensing device or cartridge 2505 further comprises a trapped segment of air 2575 between a terminus 2580 of the downstream region 2570 of the first channel 2525 and the recombination junction 2545. In some embodiments, a volume of the trapped segment of air 2575 is in the range from 0.1 μL to 10 or from 0.5 μL to 5.0 for example about 5.0 μL.

In various embodiments, a method of performing an assay on a fluid sample with a sensor in the disposable cartridge 2505 configuration is provided for that mitigates the drift of fluid samples over a sensor by incorporating a bypass channel into the microfluidics. The method comprises introducing a fluid sample through the entry port and into the holding chamber 2515, and activating a pump (e.g., the deformable member 2455, as described with respect to FIG. 24A or 24B) to create pressure to push the fluid sample from the holding chamber 2515 through the bifurcation junction 2520 into the first channel 2525 (e.g., a sensor channel) and the second channel 2530 (e.g., a bypass channel). Initially the fluid sample preferentially fills the first channel 2525 because a cross-sectional area of the second channel 2530 is less than a cross-sectional area of an upstream region 2565 of the first channel 2525, and once the upstream region 2565 of the first channel 2525 is filled with the fluid sample, then the fluid sample preferentially fills the second channel 2530 because the cross-sectional area of the second channel 2530 is greater than a cross-sectional area of a downstream region 2570 of the first channel 2525.

In some embodiments, the pumped fluid sample in the first channel 2525 and the second channel 2530 stops short of the recombination junction 2545 of the first channel 2525 and the second channel 2530. In some embodiments, the pumped fluid sample in the second channel 2530 reaches the recombination junction 2545 before the pumped fluid sample in the first channel 2525, which traps a segment of air 2575 between a terminus of the downstream region 2570 of the first channel 2525 and the recombination junction 2545. Optionally, the pressure also pushes the fluid sample through a constriction or capillary stop (e.g., the constriction or capillary stop 2487 as described with respect to FIG. 24A or 24B) to the bifurcation junction 2520. In some embodiments, the method may further include detecting that the fluid sample is over the one or more sensors 2556 using conductometric sensors. In some embodiments, this may further include performing an assay on the fluid sample over the one or more sensors 2556.

In alternative embodiments, the pumped fluid sample in the first channel 2525 and the second channel 2530 stops short of the first terminal end 2552 and the second terminal end 2554, respectively. In some embodiments, the pumped fluid sample in the second channel 2530 reaches the second terminal end 2554 before the pumped fluid sample in the first channel 2525 reaches the first terminal end 2552. Optionally, the pressure also pushes the fluid sample through a constriction or capillary stop (e.g., the constriction or capillary stop 2487 as described with respect to FIG. 24A or 24B) to the bifurcation junction 2520. In some embodiments, the method may further include detecting that the fluid sample is over the one or more sensors 2556 using conductometric sensors. In some embodiments, this may further include performing an assay on the fluid sample over the one or more sensors 2556.

In some embodiments, the method of performing the assay may further include providing or obtaining the disposable cartridge 2505, which comprises: the fluid sample entry port and the holding chamber 2515 connected to the bifurcation junction 2520 of the first channel 2525 and the second channel 2530. The first channel 2525 and the second channel 2530 may be connected at a recombination junction 2545 to the third channel 2550. The first channel 2525 may comprise the upstream region 2565 and the downstream region 2570, and the one or more sensors 2556 in the upstream region 2565. A cross-sectional area of the upstream region 2565 of the first channel 2525 may be larger than a cross-sectional area of the downstream region 2570 of the first channel 2525. A cross-sectional area of the second channel 2530 may be less than the cross-sectional area of the upstream region 2565 of the first channel 2525, and a cross-sectional area of the second channel 2530 may be greater than the cross-sectional area of the downstream region 2570 of the first channel 2525. The holding chamber 2515 may be connected to the pump (e.g., the deformable member 2455, as described with respect to FIG. 24A or 24B).

In some embodiments, the method of performing the assay may further include providing or obtaining the disposable cartridge 2505, which comprises: the fluid sample entry port and the holding chamber 2515 connected to the bifurcation junction 2520 of the first channel 2525 and the second channel 2530. The first channel 2525 may terminate at the first terminal end 2552 and the second channel 2530 terminates at a second terminal end 2554. The first channel 2525 may comprise the upstream region 2565 and the downstream region 2570, and the one or more sensors 2556 in the upstream region 2565. A cross-sectional area of the upstream region 2565 of the first channel 2525 may be larger than a cross-sectional area of the downstream region 2570 of the first channel 2525. A cross-sectional area of the second channel 2530 may be less than the cross-sectional area of the upstream region 2565 of the first channel 2525, and a cross-sectional area of the second channel 2530 may be greater than the cross-sectional area of the downstream region 2570 of the first channel 2525. The holding chamber 2515 may be connected to the pump (e.g., the deformable member 2455, as described with respect to FIG. 24A or 24B).

In some embodiments, the disposable cartridge 2505 is configured for performing diagnostic clotting time tests. In order for the disposable cartridge 2505 to be configured for performing diagnostic clotting time tests, each of the one or more sensors 2556 comprises at least one transducer coated with a polymer layer. The polymer layer may be a porous support layer that comprises immobilized therein a thrombin-cleavable peptide. The thrombin-cleavable peptide may comprise a detectable moiety linked by a thrombin-cleavable amide bond to a polypeptide sequence that is non-reactive with blood proteases other than thrombin. In certain embodiments, the one or more sensors 2556 comprise a micro-environment prothrombin time (PT) sensor disposed in a first region of the upstream region 2565 of the first channel 2525 and a micro-environment activated partial thromboplastin time (aPTT) sensor disposed in a second region of the upstream region 2565 of the first channel 2525. In other embodiments, micro-environment activated clotting time (ACT) sensor is disposed in the second region of the upstream region 2565 of the first channel 2525 as a substitute for the aPTT sensor.

In some embodiments, performing the assay on the fluid sample over the one or more sensors 2556 includes amending the fluid sample with a reagent in the first region and a reagent in the second region, waiting a predetermined amount of time for the amended fluid sample to diffuse into an immobilized substrate, in the first region and an immobilized substrate, in the second region (where the immobilized substrates may be the same or different substrate), and determining a PT using the PT sensor, and an aPTT using the aPTT sensor. In certain embodiments, performing the assay on the fluid sample over the one or more sensors 2556 includes amending the fluid sample with a PT reagent in the first region and an aPTT reagent in the second region, waiting a predetermined amount of time for the amended fluid sample to diffuse into a first thrombin-cleavable peptide, which is an immobilized PT substrate, in the first region and a second thrombin-cleavable peptide, which is an immobilized aPTT substrate, in the second region, and determining a PT using the PT sensor, and an aPTT using the aPTT sensor. During the waiting the predetermined amount of time, the fluid sample is mitigated from drifting off the PT sensor and the aPTT sensor by the presence of the second channel 2530.

Figure 26A:
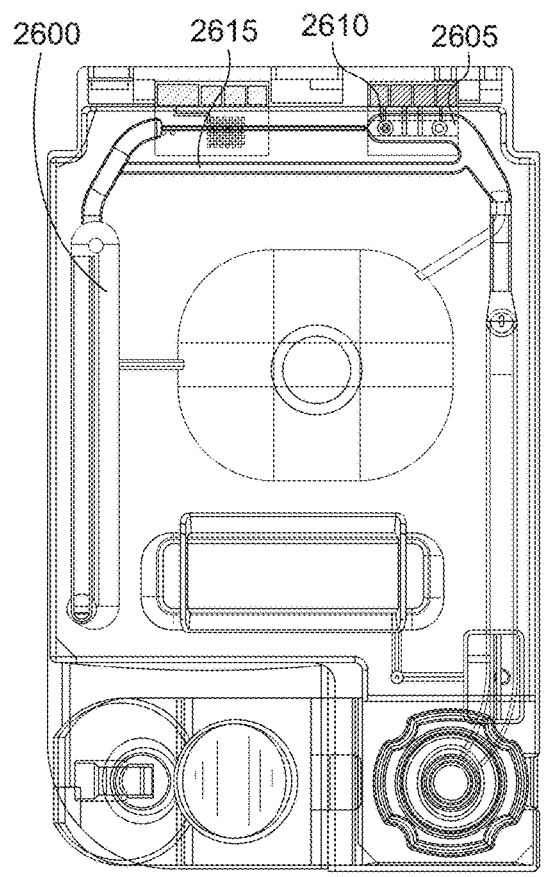
FIG. 26A shows a test cartridge device comprising a sensor channel having a micro-environment sensor structure and a bypass channel in accordance with various embodiments.
Figure 26B:
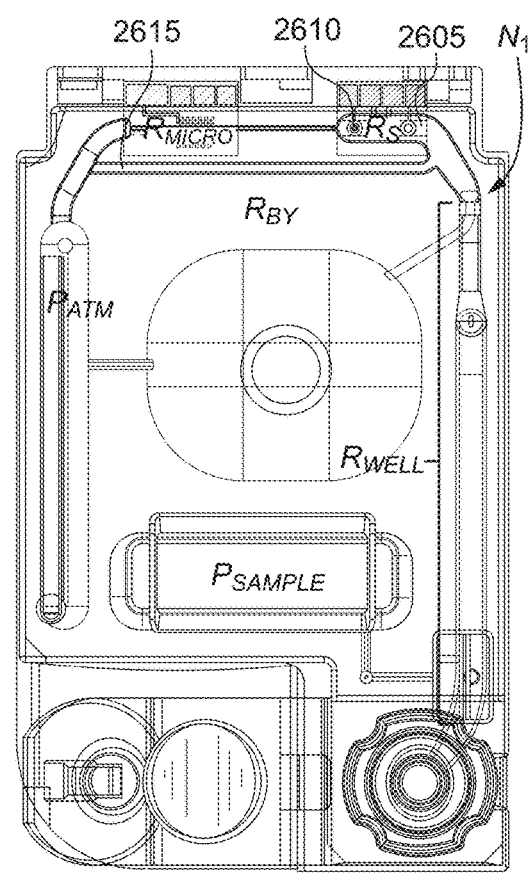
FIG. 26B shows fluidic circuit elements of test cartridge devices comprising a sensor channel having a micro-environment sensor structure and a bypass channel in accordance with various embodiments.

Application of the aforementioned assumptions and analogies between microfluidic circuits and electrical circuits are demonstrated in FIGS. 26A, 26B, 26C, 26D, and 26E for a self-contained disposable sensing device or cartridge in accordance with various aspects disclosed herein (e.g., a self-contained disposable sensing device or cartridge 2505 as described with respect to FIGS. 25A and 25B). FIG. 26A shows a test cartridge device 2600 comprising a first channel 2605 (e.g., a sensor channel) having one or more sensors 2610 and a second channel 2615 (e.g., a bypass channel) that acts as a bypass to relieve pressure from the first channel 2605. FIG. 26B shows the fluidic circuit elements of the test cartridge device 2600 including: (i) $R_{WELL}$, which is the combined or series hydraulic resistance of the sample well and channel(s)/feature(s) leading to one or more sensors, (ii) $R_S$, which is the hydraulic resistance of the upstream region of the first channel above the one or more sensors, (iii) $R_{MICRO}$, which is the hydraulic resistance of the downstream region of the first channel after the one or more sensors, (iii) $R_{BY}$, which is the hydraulic resistance of the second channel (e.g., the bypass channel), (iv) $P_{SAMPLE}$, which is the pressure generated during sample push by a pump, and (v) $P_{ATM}$, which is the atmospheric pressure.

Figure 26C:
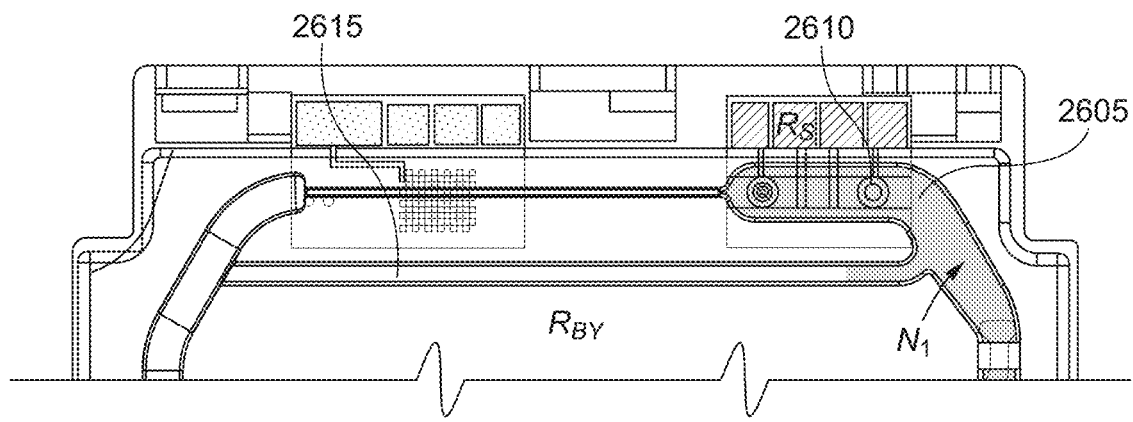
FIGS. 26C, 26D, and 26E show use of a bypass channel to relieve pressure from a sensor channel in accordance with various embodiments.
Figure 26D:
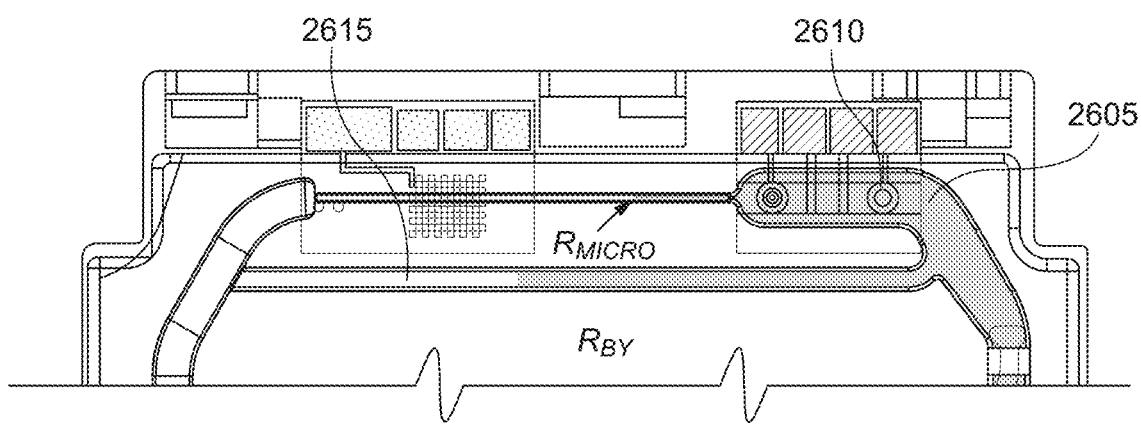
Figure 26E:
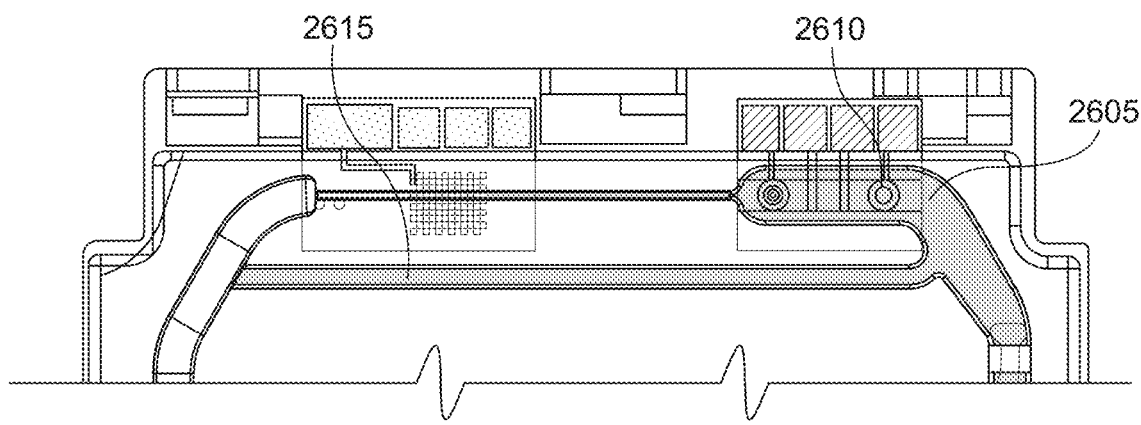

To start the assay, the air bladder is compressed to create pressure ($P_{SAMPLE}$). $P_{SAMPLE}$ is sufficient to overcome $R_{WELL}$ and move the sample to the Node ($N_J$) (e.g., a bifurcation junction). When the sample arrives at $N_J$, volumetric flow is divided according to relative resistances. As the cross-sectional area of the upstream region of the first channel 2605 is larger than the cross-sectional area of the bypass channel 2615 ($R_S<R_{BY}$), most, not all, sample flow goes into the first channel 2605, as shown in FIG. 26C. Prior to end of $P_{SAMPLE}$, the upstream region of the first channel 2605 has filled preferentially. Thereafter, sample arrives at the downstream region of the first channel 2605. The sample is now present above the one or more sensors 2610, as shown in FIG. 5C. The analyzer stops generating $P_{SAMPLE}$ either once or at a predetermined time after conductivity data from conductometric sensors around the one or more sensors 2610 indicate the one or more sensors 2610 are covered with sample. As the cross-sectional area of the downstream region is smaller than the cross sectional area of the second channel 2615 ($R_{MICRO}>R_{BY}$) and flow is divided according to relative resistances, most, not all, excess pressure and sample flow enter the second channel 2615, as shown in FIG. 26D. The second channel 2615 continues to be the preferred path for excess sample flow and pressure, and thus sample drift above the one or more sensors 2610 is mitigated, as shown in FIG. 26E.

Figure 27A:
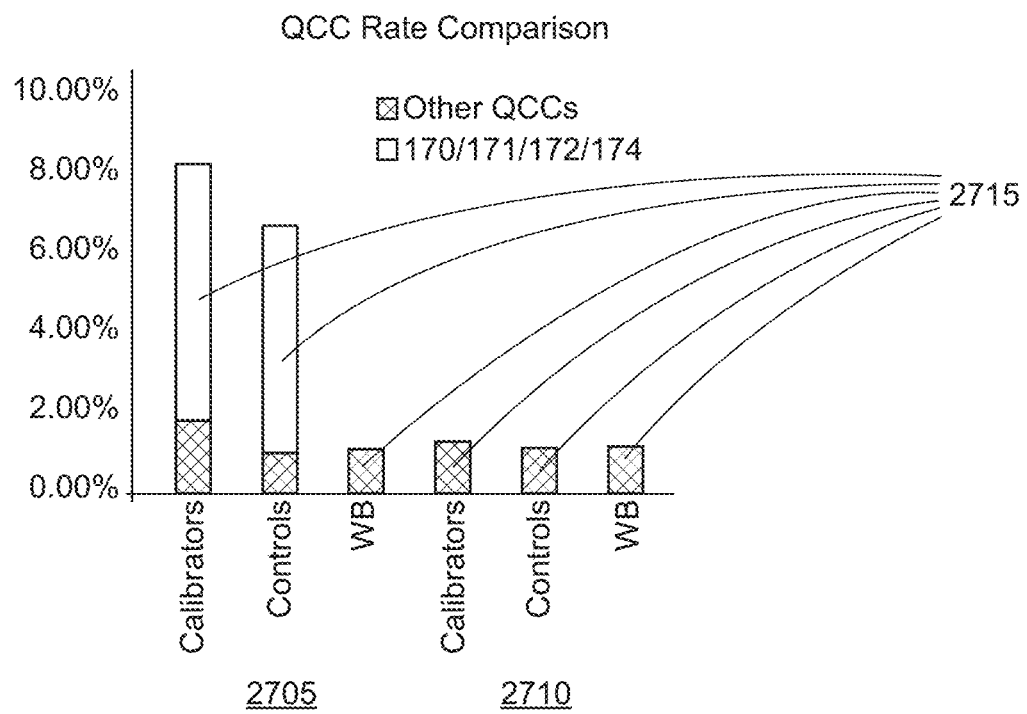
FIG. 27A shows a comparison of quality check codes (QCC) performance between conventional test cartridge devices with a sensor channel, and test cartridge devices with a sensor channel and a bypass channel in accordance with various embodiments.
Figure 27B:
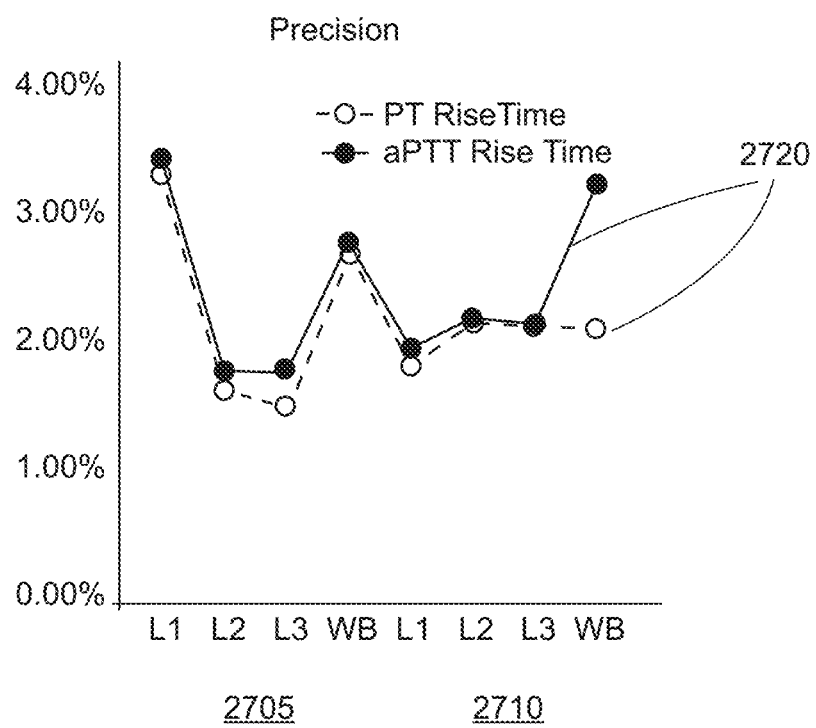
FIG. 27B shows a comparison of precision performance between conventional test cartridge devices with a sensor channel, and test cartridge devices with a sensor channel and a bypass channel in accordance with various embodiments.

FIG. 27A shows a comparison of quality check codes (QCC) (i.e., error codes displayed by the analyzer during testing) performance between test cartridge devices 2705 with a sensor channel, and test cartridge devices 2710 with a sensor channel and a bypass channel. As shown, the incidents 2715 of quality check codes significantly dropped in test cartridge devices 2710 with a sensor channel and a bypass channel, which were designed in accordance with various aspects discussed herein. FIG. 27B shows a comparison of precision in PT and aPTT testing performance between conventional test cartridge devices 2705 with a single sensor channel, and test cartridge devices 2710 with a sensor channel and a bypass channel. As shown, the precision 2720 of PT and aPTT testing significantly performed better (e.g., L1 was much more precise) in test cartridge devices 2710 with a sensor channel and a bypass channel, which were designed in accordance with various aspects discussed herein.

While the invention has been described in detail, modifications within the spirit and scope of the invention will be readily apparent to the skilled artisan. It should be understood that aspects of the invention and portions of various embodiments and various features recited above and/or in the appended claims may be combined or interchanged either in whole or in part. In the foregoing descriptions of the various embodiments, those embodiments which refer to another embodiment may be appropriately combined with other embodiments as will be appreciated by the skilled artisan. Furthermore, the skilled artisan will appreciate that the foregoing description is by way of example only, and is not intended to limit the invention.

What is claimed is:

1. A test cartridge device for measuring an analyte in a fluid sample, the test cartridge device comprising:
   a fluid sample entry port for receiving the fluid sample;
   a holding chamber fluidically connected to the entry port;
   a bifurcation junction fluidically connected to the holding chamber;
   a first channel splitting off from the bifurcation junction, the first channel comprising an upstream region and a downstream region;
   a sensor positioned within the upstream region for measuring the analyte in the fluid sample;
   a second channel splitting off from the bifurcation junction; and
   a recombination junction that rejoins the first channel and the second channel into a third channel,
   wherein a cross-sectional area of the upstream region is greater than a cross-sectional area of the downstream region; and
   wherein a cross-sectional area of the second channel is less than the cross-sectional area of the upstream region and greater than the cross-sectional area of the downstream region, which structurally configures the second channel as an additional resistive element that is configured to act as a preferred path for excess fluid sample flow and pressure when the fluid sample reaches the cross-sectional area of the downstream region of the first channel.

2. The test cartridge device of claim 1, wherein a ratio of the cross-sectional area of the upstream region to the cross-sectional area of the downstream region is in a range from 4:1 to 50:1.

3. The test cartridge device of claim 1, wherein a ratio of the cross-sectional area of the second channel to the cross-sectional area of the upstream region is in a range from 0.5:1 to 1:125 and a ratio of the cross-sectional area of the second channel to the cross-sectional area of the downstream region is in a range from 1.2:1 to 100:1.

4. The test cartridge device of claim 1, wherein the cross-sectional area of the upstream region is in a range from 0.1 mm$^2$ to 20 mm$^2$.

5. The test cartridge device of claim 1, wherein the cross-sectional area of the downstream region is in a range from 0.1 mm$^2$ to 10 mm$^2$.

6. The test cartridge device of claim 1, wherein the cross-sectional area of the second channel is in a range from 0.1 mm² to 15 mm².

7. The test cartridge device of claim 1, wherein a volume of the upstream region is in a range from 0.5 µL to 50 µL.

8. The test cartridge device of claim 1, wherein a volume of the downstream region is in a range from 0.5 µL to 50 µL.

9. The test cartridge device of claim 1, wherein a volume of the second channel is in a range from 0.5 µL to 50 µL.

10. The test cartridge device of claim 1, wherein a total volume of the first channel from the bifurcation junction to the recombination junction is in a range from 0.5 µL to 50 µL.

11. The test cartridge device of claim 1, wherein the third channel comprises a vent to an atmosphere outside of the test cartridge device.

12. The test cartridge device of claim 1, further comprising a lead channel that joins the bifurcation junction with the holding chamber.

13. The test cartridge device of claim 12, further comprising constriction or capillary stop at a terminus of the holding chamber.

14. The test cartridge device of claim 13, wherein the lead channel defines a channel area between the constriction or capillary stop and the bifurcation junction.

15. The test cartridge device of claim 1, wherein the sensor comprises one or more transducers coated with a polymer layer, the polymer layer is a porous support layer that comprises immobilized therein a thrombin-cleavable peptide, and the thrombin-cleavable peptide comprises a detectable moiety linked by a thrombin-cleavable amide bond to a polypeptide sequence that is non-reactive with blood proteases other than thrombin.

16. The test cartridge device of claim 15, wherein the sensor is a prothrombin time (PT) sensor, an activated partial thromboplastin time (aPTT) sensor, or an activated clotting time (ACT) sensor.

17. A test system comprising:
an instrument; and
a test cartridge device electrically connected to the instrument,
wherein the test cartridge device comprises a fluid sample entry port and a holding chamber connected to a bifurcation junction of a first channel and a second channel,
wherein the first channel comprises an upstream region and a downstream region,
wherein at least one analyte sensor is in the upstream region,
wherein a cross-sectional area of the upstream region of the first channel is larger than a cross-sectional area of the downstream region the first channel,
wherein a cross-sectional area of the second channel is less than the cross-sectional area of the upstream region of the first channel, and
wherein the cross-sectional area of the second channel is greater than the cross-sectional area of the downstream region of the first channel, which structurally configures the second channel as an additional resistive element that is configured to act as a preferred path for excess fluid sample flow and pressure when a fluid sample reaches the cross-sectional area of the downstream region of the first channel.

18. The test system of claim 17, wherein a ratio of the cross-sectional area of the upstream region to the cross-sectional area of the downstream region is in a range from 4:1 to 50:1.

19. The test system of claim 17, wherein a ratio of the cross-sectional area of the second channel to the cross-sectional area of the upstream region is in a range from 0.5:1 to 1:125 and a ratio of the cross-sectional area of the second channel to the cross-sectional area of the downstream region is in a range from 1.2:1 to 100:1.

20. A method for measuring an analyte in a fluid sample, the method comprising:
introducing the fluid sample through an entry port and into a holding chamber, wherein the fluid sample entry port and the holding chamber are connected to a bifurcation junction of a first channel and a second channel;
activating a pump to create pressure to push the fluid sample from the holding chamber through the bifurcation junction into the first channel and the second channel, wherein initially the fluid sample preferentially fills the first channel because a cross-sectional area of the second channel is less than a cross-sectional area of an upstream region of the first channel, and once the upstream region of the first channel is filled with the fluid sample, then the fluid sample preferentially fills the second channel to relieve excess pressure because the cross-sectional area of the second channel is greater than a cross-sectional area of a downstream region of the first channel; and
performing an assay on the fluid sample in contact with a sensor in the upstream region of the first channel in order to measure the analyte in the fluid sample, wherein the relief of the excess pressure when the fluid sample fills the upstream region of the first channel and reaches the cross-sectional area of the downstream region of the first channel acts to mitigate fluid sample drift and allows for the fluid sample to sit over the sensor and complete performance of the assay.

* * * * *